(12) United States Patent
Nielsen et al.

(10) Patent No.: US 11,911,375 B2
(45) Date of Patent: Feb. 27, 2024

(54) SOLID ORAL NICOTINE FORMULATION

(71) Applicant: Fertin Pharma A/S, Vejle (DK)

(72) Inventors: Kent Albin Nielsen, Brande (DK); Jessie Poulsen, Odense SV (DK)

(73) Assignee: FERTIN PHARMA A/S, Vejle (DK)

( * ) Notice: Subject to any disclaimer, the term of this patent is extended or adjusted under 35 U.S.C. 154(b) by 246 days.

(21) Appl. No.: 17/098,550

(22) Filed: Nov. 16, 2020

(65) Prior Publication Data

US 2022/0152013 A1    May 19, 2022

(51) Int. Cl.
| | |
|---|---|
| *A61K 31/465* | (2006.01) |
| *A61K 9/68* | (2006.01) |
| *A61K 9/20* | (2006.01) |
| *A61K 47/02* | (2006.01) |
| *A61K 47/14* | (2017.01) |
| *A61K 47/26* | (2006.01) |
| *A61K 47/32* | (2006.01) |
| *A61K 47/44* | (2017.01) |

(52) U.S. Cl.
CPC .......... *A61K 31/465* (2013.01); *A61K 9/0058* (2013.01); *A61K 9/2009* (2013.01); *A61K 9/2018* (2013.01); *A61K 9/2027* (2013.01); *A61K 9/2054* (2013.01); *A61K 9/2059* (2013.01); *A61K 9/2068* (2013.01); *A61K 47/02* (2013.01); *A61K 47/14* (2013.01); *A61K 47/26* (2013.01); *A61K 47/32* (2013.01); *A61K 47/44* (2013.01)

(58) Field of Classification Search
CPC .................................................. A61K 31/465
See application file for complete search history.

(56) References Cited

U.S. PATENT DOCUMENTS 9,585,967 B2 * 3/2017 Franz ...................... A61P 25/26

FOREIGN PATENT DOCUMENTS

| | | | | |
|---|---|---|---|---|
| EP | 2198865 | * | 12/2008 | ............. A61K 47/18 |
| EP | 2198865 A1 | | 6/2010 | |
| EP | 2152313 | * | 9/2014 | ............. A61K 47/18 |
| EP | 2152313 B1 | | 9/2014 | |
| WO | WO2004/004478 A1 | | 1/2004 | |
| WO | WO2004/004479 A1 | | 1/2004 | |
| WO | WO 2020157280 | * | 8/2020 | ............. A24B 13/00 |

OTHER PUBLICATIONS

Partial International Search Report dated Feb. 23, 2022 in International Application No. PCT/DK2021/050335, 3 pages.

* cited by examiner

*Primary Examiner* — Nizal S Chandrakumar
(74) *Attorney, Agent, or Firm* — Lee & Hayes P.C.

(57) ABSTRACT

A solid oral nicotine formulation is disclosed, the formulation comprises a nicotine-ion exchange resin combination, and a salt comprising inorganic divalent cations, wherein the salt has a water-solubility of at least 5 grams per 100 mL of water measured at 25 degrees Celsius, atmospheric pressure and pH 7.0.

17 Claims, No Drawings

SOLID ORAL NICOTINE FORMULATION

FIELD OF INVENTION

The present invention relates to solid oral nicotine formulations according to the claims.

BACKGROUND

Delivery of nicotine by smoking has many well-known drawbacks, in particular health related problems, such as inclusion of carcinogenic substances.

However, tobacco substitutes also suffer from disadvantages, such as inadequate relief of cravings for the user.

A further challenge in the prior art is that the desired release of nicotine should be attractive to the user of the nicotine formulation from a user perspective.

Yet at further challenge in relation to the prior art may be that nicotine formulation as delivery vehicle for nicotine may be somewhat costly and thereby impose restrictions on the way nicotine formulation are designed in order to keep manufacturing costs in check.

It is an object of one embodiment of the present invention to provide a solid oral nicotine formulation, e.g. as a tobacco substitute, which may solve the above problems.

SUMMARY

The invention relates to a solid oral nicotine formulation comprising
a nicotine-ion exchange resin combination,
and a salt comprising inorganic divalent cations,
wherein the salt has a water-solubility of at least 5 grams per 100 mL of water measured at 25 degrees Celsius, atmospheric pressure and pH 7.0.

One advantage of the present invention may be that a relatively high stability of the provided nicotine may be obtained, while at the same time obtaining a relatively fast nicotine release. Obtaining a high stability may lead to nicotine being bound too effectively e.g. to a carrier and therefore lead to slow release. By means of the claimed solid oral nicotine formulation, including salt comprising divalent inorganic cations, a high stability yet fast release is facilitated.

A further advantage of the invention is that a relatively high release rate of nicotine from the solid oral nicotine formulation may be obtained due to the presence of the salt comprising inorganic divalent cations and having a sufficient water-solubility. The fast release of nicotine advantageously provides for a fast relief of nicotine craving for the users.

Even further the invention may advantageously provide a more effective release of nicotine during use of the solid oral nicotine formulation. Obtaining an effective release of nicotine may enable a lower total dose of nicotine with the same amount of nicotine released, due to a minimization of any residual nicotine not released from the solid oral nicotine formulation.

In an advantageous embodiment of the invention, the solid oral nicotine formulation comprises said salt in the amount of between 0.1 and 15.0% by weight of the composition, such as between 0.1 and 10.0% by weight of the composition, such as between 0.5 and 10.0% by weight of the composition.

In an embodiment of the invention the solid oral nicotine formulation comprises salt in an amount of between 0.1 and 15.0% by weight of the composition, such as between 0.1 and 10.0% by weight of the composition, such as between 0.5 and 7.0% by weight of the composition, such as between 0.1 and 7.0% by weight of the composition, such as between 0.5 and 5.0% by weight of the composition, such as between 0.5 and 4.0% by weight of the composition.

Here, the amount of salt is based on the molecular weight of the anhydrous salt. However, the salt may be provided as a hydrated salt.

In an advantageous embodiment of the invention, the solid oral nicotine formulation comprises divalent cations in molar ratio of at least 0.1 relative to the amount of nicotine in the nicotine-ion exchange resin combination, such as at least 0.25 relative to the amount of nicotine in the nicotine-ion exchange resin combination, such as at least 0.5 relative to the amount of nicotine in the nicotine-ion exchange resin combination.

The amount of divalent cations should advantageously be high enough to enable ion-exchange of the complexed nicotine for the divalent cations during use of the solid oral nicotine formulation.

Furthermore, the amount of divalent cations may advantageously also decrease the probability of exchanged nicotine from re-complexing with the ion-exchange resin, simply by occupying binding sites on the ion-exchange resin during use.

In an embodiment of the invention the amount of divalent cations may even prevent exchanged nicotine from re-complexing with the ion-exchange resin during use.

Also, the amount of divalent cations may decrease the probability of any un-complexed nicotine, such as free base nicotine and/or exchanged nicotine from complexing/re-complexing with the ion-exchange resin during use.

In an advantageous embodiment of the invention, the solid oral nicotine formulation comprises divalent cations in a molar ratio of at most 10 relative to the amount of nicotine in the nicotine-ion exchange resin combination, such as at most 5 relative to the amount of nicotine in the nicotine-ion exchange resin combination, such as at most 3.75 relative to the amount of nicotine in the nicotine-ion exchange resin combination, such as at most 2.5 relative to the amount of nicotine in the nicotine-ion exchange resin combination.

One advantage of the above embodiment may be that including divalent cations in a not too high amount facilitates a desirable taste and mouthfeel, by avoiding or minimizing undesirable taste and/or mouthfeel, such as a local dehydration or even an oral dehydrating sensation. Thus, the solid oral nicotine formulation may provide a desirable release rate of nicotine while at the same time also a desirable taste and mouthfeel.

In an embodiment of the invention the solid oral nicotine formulation comprises divalent cations in a molar ratio of between 0.1 and 10.0 relative to the amount of nicotine in the nicotine-ion exchange resin combination, such as between 0.1 and 7.0 relative to the amount of nicotine in the nicotine-ion exchange resin combination, such as between 0.1 and 5.0 relative to the amount of nicotine in the nicotine-ion exchange resin combination, such as between 0.1 and 4.0 relative to the amount of nicotine in the nicotine-ion exchange resin combination, such as between 0.1 and 3.0 relative to the amount of nicotine in the nicotine-ion exchange resin combination, such as between 0.1 and 2.0 relative to the amount of nicotine in the nicotine-ion exchange resin combination, such as between 0.1 and 1.0 relative to the amount of nicotine in the nicotine-ion exchange resin combination.

In an embodiment of the invention the solid oral nicotine formulation comprises divalent cations in a molar ratio of between 0.1 and 10.0 relative to the amount of nicotine in the nicotine-ion exchange resin combination, such as between 0.1 and 7.0 relative to the amount of nicotine in the nicotine-ion exchange resin combination, such as between 0.1 and 5.0 relative to the amount of nicotine in the nicotine-ion exchange resin combination, such as between 0.5 and 5.0 relative to the amount of nicotine in the nicotine-ion exchange resin combination, such as between 0.75 and 5.0 relative to the amount of nicotine in the nicotine-ion exchange resin combination, such as between 1.0 and 4.0 relative to the amount of nicotine in the nicotine-ion exchange resin combination, such as between 2.0 and 4.0 relative to the amount of nicotine in the nicotine-ion exchange resin combination.

In an embodiment of the invention the solid oral nicotine formulation comprises divalent cations in a molar ratio of between 0.01 and 5.0 relative to the amount of nicotine in the nicotine-ion exchange resin combination, such as between 0.01 and 4.0 relative to the amount of nicotine in the nicotine-ion exchange resin combination, such as between 0.01 and 3.0 relative to the amount of nicotine in the nicotine-ion exchange resin combination, such as between 0.01 and 2.0 relative to the amount of nicotine in the nicotine-ion exchange resin combination, such as between 0.01 and 1.0 relative to the amount of nicotine in the nicotine-ion exchange resin combination.

Here, the molar ratio refers to the molar content of divalent cations divided by the molar content of nicotine.

In an advantageous embodiment of the invention, the divalent cations are selected from the group consisting of divalent cations of calcium, magnesium, iron, zinc, and any combination thereof.

In an advantageous embodiment of the invention, the divalent cations are selected from the group consisting of divalent cations of calcium and magnesium.

In an advantageous embodiment of the invention, the salt comprises anions selected from the group consisting of carboxylates, such as formate, acetate, lactate, propionate, or levulinate; organic sulfonate; organic sulfate; organic phosphate; chloride, bromide, nitrate, sulfate, hydrogen carbonate, and any combination thereof.

In an embodiment of the invention the salt comprises anions selected from the group consisting of carboxylates, such as acetate, lactate, propionate, or levulinate; organic sulfonate; organic sulfate; organic phosphate; chloride, bromide, nitrate, sulfate, hydrogen carbonate, and any combination thereof.

In an embodiment of the invention, the organic anions are selected from the group consisting of carboxylates, such as formate, acetate, lactate, propionate, levulinate; organic sulfonate; organic sulfate; organic phosphate; and any combination thereof.

In an advantageous embodiment of the invention, the salt is an inorganic salt.

In an advantageous embodiment of the invention, the solid oral nicotine formulation comprises inorganic salt in an amount of between 0.1 and 15.0% by weight of the composition, such as between 0.1 and 10.0% by weight of the composition, such as between 0.5 and 10.0% by weight of the composition.

In an embodiment of the invention the solid oral nicotine formulation comprises inorganic salt in an amount of between 0.1 and 15.0% by weight of the composition, such as between 0.1 and 10.0% by weight of the composition, such as between 0.5 and 7.0% by weight of the composition, such as between 0.1 and 7.0% by weight of the composition, such as between 0.5 and 5.0% by weight of the composition, such as between 0.5 and 4.0% by weight of the composition.

In an advantageous embodiment of the invention, the salt comprises inorganic anions selected from the group consisting of chloride, bromide, nitrate, sulfate, hydrogen carbonate, and any combination thereof.

In an advantageous embodiment of the invention, the salt comprises inorganic anions selected from the group consisting of chloride, bromide, sulfate, hydrogen carbonate, and any combination thereof.

In an advantageous embodiment of the invention, the salt comprises inorganic anions selected from the group consisting of chloride, bromide, sulfate, and any combination thereof.

In an advantageous embodiment of the invention, the salt comprises inorganic anions selected from the group consisting of chloride, bromide, and any combination thereof.

One advantage of the above embodiment may be that desirable characteristics is facilitated e.g. with respect to obtaining a high water solubility, providing an acceptable taste and mouthfeel etc.

In an advantageous embodiment of the invention, the salt comprises chloride.

In an embodiment of the invention, the inorganic divalent cations are magnesium and/or calcium and the anions comprise chloride.

In an embodiment of the invention, the inorganic anions are chloride.

In an advantageous embodiment of the invention, the salt is selected from the group consisting of calcium chloride and magnesium chloride, or combinations thereof.

In an embodiment of the invention, the inorganic divalent cations are magnesium and/or calcium and the anions are chloride.

In an embodiment of the invention the salt is magnesium chloride and/or calcium chloride.

One advantage of the above embodiment may be that desirable characteristics is facilitated e.g. with respect to obtaining a high water solubility, providing an acceptable taste and mouthfeel etc.

In an embodiment of the invention the salt is provided as a hydrated salt.

In an embodiment of the invention the salt is provided as a hydrated inorganic salt.

In an embodiment of the invention, salt is provided as a pharmaceutically acceptable salt.

In an embodiment of the invention, salt is provided as a pharmaceutically acceptable inorganic salt. With provided is here understood, that the inorganic cations are added to the composition as a salt.

An advantage of the above embodiment that be a faster and more effective dissolution of the salt is obtained i.e. a faster and more effective dissolution into ions, which may facilitate a relatively fast release rate of nicotine.

In an advantageous embodiment of the invention, the solid oral nicotine formulation comprises nicotine in an amount of at least 0.1% by weight, such as least 0.2% by weight of the solid oral nicotine formulation composition.

In an embodiment of the invention, the solid oral nicotine formulation comprises nicotine in an amount of 0.1 to 5.0% by weight of the solid oral nicotine formulation, such as 0.2 to 4.0% by weight of the solid oral nicotine formulation, such as 1.0 to 2.0% by weight of the solid oral nicotine formulation.

In an advantageous embodiment of the invention, the solid oral nicotine formulation comprises nicotine in an amount of less than 5% by weight, such as less than 3% by weight, such as less than 2% by weight.

The invention may facilitate fast release of nicotine, but at the same time provide an effective release of nicotine, thereby a sustained craving relief, which is very effective. Having a very effective craving relief may further provide a reduction of necessary nicotine dose of the solid oral formulation, without compromising the resulting effect. A lower nicotine dose may in tern result in a reduction in production cost, as nicotine may be relatively expensive, but may also assist users who want to lower their intake of nicotine.

In an embodiment of the invention, the solid oral nicotine formulation comprises nicotine in an amount of less than 5% by weight.

In an advantageous embodiment of the invention, the solid oral nicotine formulation comprises nicotine in an amount of between 0.1 mg and 20.0 mg, such as 0.1 and 8.0 mg, such as 0.2 and 6.0 mg, such as 0.5 and 4.0 mg.

In an advantageous embodiment of the invention, the solid oral nicotine formulation comprises nicotine-ion exchange combination in an amount of between 1 and 100 mg.

In an embodiment of the invention, the solid oral nicotine formulation comprises nicotine-ion exchange combination in an amount of between 1 and 100 mg, such as between 1 and 70 mg, such as between 1 and 50 mg, such as between 10 and 50 mg, such as between 30 and 50 mg.

In an embodiment of the invention, the solid oral nicotine formulation comprises nicotine-ion exchange combination in an amount of between 1 and 50 mg, such as between 1 and 40 mg, such as between 1 and 30 mg, such as between 1 and 20 mg, such as between 1 and 10 mg.

In an advantageous embodiment of the invention, the solid oral nicotine formulation comprises nicotine-ion exchange combination in an amount of between 0.1 and 20% by weight.

In an embodiment of the invention, the solid oral nicotine formulation comprises nicotine-ion exchange combination in an amount of between 0.1 and 20% by weight, such as between 0.5 and 15% by weight, such as between 0.5 and 12% by weight, such as between 1 and 10% by weight.

In an embodiment of the invention, the solid oral nicotine formulation comprises nicotine-ion exchange combination in an amount of between 0.1 and 20% by weight, such as between 0.1 and 10% by weight, such as between 0.1 and 7% by weight, such as between 0.1 and 5% by weight, such as between 0.1 and 3% by weight.

In an embodiment of the invention the solid oral nicotine formulation comprises further nicotine.

In an advantageous embodiment of the invention, the solid oral nicotine formulation comprises further nicotine.

In an advantageous embodiment of the invention, the solid oral nicotine formulation comprises further nicotine selected from the group consisting of a nicotine salt, nicotine free base, nicotine bound to an ion exchanger, such as an ion exchange resin, such as nicotine polacrilex resin, a nicotine inclusion complex or nicotine in any non-covalent binding; nicotine bound to zeolites; nicotine bound to cellulose, such as microcrystalline cellulose, or starch microspheres, and mixtures thereof.

In an advantageous embodiment of the invention, the nicotine-ion exchange resin combination comprises nicotine in an amount of between 5 and 50% by weight.

In an embodiment of the invention the nicotine-ion exchange resin combination comprises nicotine complexed with ion exchange resin, wherein the nicotine constitutes an amount of between 5 and 50% by weight of nicotine-ion exchange resin combination.

In an embodiment of the invention the nicotine-ion exchange resin combination consist of nicotine complexed with ion exchange resin, wherein the nicotine constitutes an amount of between 10 and 50% by weight of nicotine-ion exchange resin combination such as between 10 and 40% by weight of nicotine-ion exchange resin combination, such as. between 10 and 30% by weight of nicotine-ion exchange resin combination, such as between 10 and 25% by weight of nicotine-ion exchange resin combination.

In an embodiment of the invention the nicotine-ion exchange resin combination comprises free-base nicotine mixed with ion exchange resin, wherein the nicotine constitutes an amount of between 5 and 50% by weight of nicotine-ion exchange resin combination, such as between 10 and 50% by weight of nicotine-ion exchange resin combination, such as between 20 and 50% by weight of nicotine-ion exchange resin combination, such as between 25 and 50% by weight of nicotine-ion exchange resin combination, such as between 25 and 45% by weight of nicotine-ion exchange resin combination.

In an embodiment of the invention the nicotine-ion exchange resin combination comprises free-base nicotine mixed with ion exchange resin, wherein the nicotine constitutes an amount of between 5 and 40% by weight of nicotine-ion exchange resin combination, such as between 10 and 40% by weight of nicotine-ion exchange resin combination, such as between 10 and 35% by weight of nicotine-ion exchange resin combination, such as between 10 and 25% by weight of nicotine-ion exchange resin combination, such as between 10 and 15% by weight of nicotine-ion exchange resin combination.

In an advantageous embodiment of the invention, the nicotine-ion exchange resin combination comprises nicotine in an amount of between 5 and 50% by weight and ion-exchange resin in an amount between 10 and 95% by weight.

In an embodiment of the invention the nicotine-ion exchange resin combination comprises nicotine in an amount of between 10 and 30% by weight and ion-exchange resin in an amount between 20 and 90% by weight.

In an embodiment of the invention the nicotine-ion exchange resin combination consists of nicotine in an amount of between 10 and 30% by weight and ion-exchange resin in an amount between 70 and 90% by weight.

In an embodiment of the invention the nicotine-ion exchange resin combination is substantially free of water.

In an embodiment of the invention, the nicotine-ion exchange resin combination further comprising a C3 sugar alcohol.

In an embodiment, the C3 sugar alcohol may be selected from glycerol, propylene glycol, and any combination thereof.

In an embodiment of the invention, the nicotine-ion exchange resin combination further comprises glycerol.

In an embodiment of the invention, the nicotine-ion exchange resin combination further comprises glycerol in an amount of 0.1 to 50% by weight, such as 5 to 40% by weight, such as 5 to 30% by weight.

In an embodiment of the invention the nicotine-ion exchange resin combination comprises nicotine in an amount of between 5 and 50% by weight and ion-exchange resin in an amount between 20 and 75% by weight.

In an embodiment of the invention the nicotine-ion exchange resin combination comprises water in an amount of no more than 75% by weight, such as no more than 50% by weight, such as no more than 50% by weight, such as no more than 40% by weight, such as no more than 30% by weight, such as no more than 20% by weight, such as no more than 10% by weight, such as no more than 5% by weight.

In an advantageous embodiment of the invention, the ion-exchange resin comprises one or more resin(s) selected from the group consisting of:
(i) a methacrylic, weakly acidic type of resin containing carboxylic functional groups,
(ii) a copolymer of methacrylic acid and divinylbenzene, said copolymer containing carboxylic functional groups,
(iii) a polystyrene, strongly acidic type of resin containing sulphonic functional groups,
(iv) a polystyrene, intermediate acidic type of resin containing phosphonic functional groups, and
(v) a combination thereof.

In an advantageous embodiment of the invention, the ion exchange resin comprises, or consists essentially of, a copolymer of methacrylic acid and divinylbenzene, said copolymer containing carboxylic functional groups.

In an advantageous embodiment of the invention, the ion exchange resin comprises polacrilex resin.

In an advantageous embodiment of the invention, the ion exchange resin is polacrilex resin.

In an embodiment of the invention, the ion exchange resin is polacrilex resin.

In an embodiment of the invention, the polacrilex resin comprises or is Amberlite®IRP64.

In an advantageous embodiment of the invention, the nicotine-ion exchange resin combination comprises nicotine complexed with ion exchange resin.

In an advantageous embodiment of the invention, the nicotine-ion exchange resin combination consists of nicotine complexed with ion exchange resin.

In an advantageous embodiment of the invention, the nicotine-ion exchange resin combination comprises free-base nicotine mixed with ion exchange resin.

In an embodiment of the invention, the nicotine-ion exchange resin combination consist of free-base nicotine mixed with ion exchange resin.

One advantage of the above embodiment may be providing sustained release of nicotine. At the same time, the release rate of nicotine is not too slow to give the user the craving relief desired.

In an advantageous embodiment of the invention, the solid oral nicotine formulation comprises water in an amount of less than 5% by weight, such as less than 4% by weight, such as less than 3% by weight, such as less than 2% by weight.

In an advantageous embodiment of the invention, the solid oral nicotine formulation has a water content of less than 5% by weight, such as less than 4% by weight, such as less than 3% by weight, such as less than 2% by weight, such as less than 1% by weight.

An advantage of the above embodiment may be that the physical stability of the solid oral nicotine formulation is increased, such as a less friable formulation or a formulation having a non-sticky surface.

Also, a low water content may advantageously decrease undesirable degradation of formulation ingredient, such as flavors and/or nicotine. Hence a more chemical stable solid oral nicotine formulation may be obtained.

In an advantageous embodiment of the invention, the solid oral nicotine formulation is essentially free of water.

In an embodiment of the invention, the solid oral nicotine formulation may be substantially free of water.

In an advantageous embodiment of the invention, the solid oral nicotine formulation further comprises a pH-regulating agent in an amount of 0.01 and 15% by weight.

Obtaining a relatively fast release rate of nicotine and an effective uptake/absorption may be desirable as this ensures a fast effect for the user, i.e. craving relief. Furthermore, the combination of having an effective release and an effective absorption advantageously enables a relative high exploitation of the nicotine dose within the solid oral nicotine formulation. Having a relative high exploitation of the nicotine dose within the solid oral nicotine formulation may further provide a reduction of necessary nicotine dose of the solid oral formulation, without compromising the resulting effect. A lower nicotine dose may in tern result in a reduction in production cost, as nicotine may be relatively expensive, but may also assist users who want to lower their intake of nicotine.

In an embodiment of the invention, the pH regulating agent is selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

In an advantageous embodiment of the invention, the pH regulating agent is selected from the group consisting Sodium carbonate, Sodium bicarbonate, Potassium carbonate, and Magnesium carbonate; Potassium bicarbonate; trometamol; phosphate buffer, or any combination thereof.

The above embodiment provides an advantageously high pH value, which may facilitate a relatively effective uptake of nicotine.

Also, the high pH value obtained may advantageously provide for a tingling sensation in the mouth which may be perceived as a desirable mouthfeel, e.g. due to resemblance with tobacco-based products.

In an embodiment, the solid oral nicotine formulation comprises water soluble salt comprising inorganic divalent cations, and in addition thereto a pH regulating agent selected from the group consisting Sodium carbonate, Sodium bicarbonate, Potassium carbonate, and Magnesium carbonate; Potassium bicarbonate; trometamol; phosphate buffer, or any combination thereof.

In the present context the term trometamol refers to (tris(hydroxymethyl)aminomethane), also sometimes referred to as tris buffer.

In an advantageous embodiment of the invention, the pH adjusting agent is trometamol.

In an advantageous embodiment of the invention, the pH adjusting agent is free of carbonates.

In an advantageous embodiment of the invention, the solid oral nicotine formulation comprises at least one sugar alcohol.

In an embodiment of the invention, xylitol, maltitol, mannitol, erythritol, isomalt, sorbitol, lactitol, and mixtures thereof is used as the at least one sugar alcohol. The at least one sugar alcohol may also comprise further sugar alcohols. As an example embodiment, hydrogenated starch hydrolysates may be used, which comprises a mixture of sorbitol, maltitol and further sugar alcohols.

In an embodiment of the invention, the at least one sugar alcohol is selected from sugar alcohols having at least 4 carbon atoms.

In an advantageous embodiment of the invention, the at least one sugar alcohol is selected from xylitol, maltitol, mannitol, erythritol, isomalt, sorbitol, lactitol, and mixtures thereof.

Sugar alcohols may advantageously facilitate and induce salivation during use of the solid oral nicotine formulation, whereby dissolution of the inorganic divalent cations are achieved, and release of nicotine is obtained, such as release of nicotine from the ion-exchange resin and release of nicotine from the formulation.

Sugar alcohols may advantageously be used to further increase the nicotine release from the solid oral nicotine formulation.

Also, sugar alcohols may advantageously be used for obtaining a desirable mouthfeel by increasing salivation.

Thus, sugar alcohol may advantageously be used in combination with inorganic divalent cations in order to achieve a desirable release of nicotine, while also a desirable taste and mouthfeel is achieved.

In an advantageous embodiment of the invention, the solid oral nicotine formulation comprises at least two sugar alcohols.

It is noted that different sugar alcohols may be applied for the purpose of taste and salivation, where the sugar alcohol composition is made of different sugar alcohols having different properties with respect to storage, bacteria growth, processability and/or taste.

In an embodiment of the invention, the at least two sugar alcohols are selected from xylitol, maltitol, mannitol, erythritol, isomalt, sorbitol, lactitol, and mixtures thereof.

In an advantageous embodiment of the invention, the solid oral nicotine formulation comprises sugar alcohol in an amount of at least 20% by weight, such as at least 30% by weight, such as at least 40% by weight, such as at least 50% by weight.

In an advantageous embodiment of the invention, the solid oral nicotine formulation comprises sugar alcohol in an amount of between 20% and 95% by weight, such as between 30 and 95% by weight, such as between 40 and 95% by weight, such as between 50 and 95% by weight.

In an embodiment of the invention, the solid oral nicotine formulation comprises sugar alcohol in an amount of between 20% and 95% by weight, such as between 50 and 95% by weight, such as between 60 and 95% by weight, such as between 70 and 95% by weight, such as between 80 and 95% by weight.

In an embodiment of the invention, the solid oral nicotine formulation comprises sugar alcohol in an amount of between 20% and 95% by weight, such as between 20 and 80% by weight, such as between 30 and 70% by weight, such as between 40 and 70% by weight.

In an embodiment of the invention, the solid oral nicotine formulation comprises sugar alcohol in an amount of between 20% and 95% by weight, such as between 40 and 95% by weight, such as between 50 and 85% by weight, such as between 60 and 85% by weight.

In an embodiment of the invention, the sugar alcohol comprises a DC (direct compressible) grade sugar alcohol.

In an embodiment of the invention, at least 50% by weight of the sugar alcohol is a DC (direct compressible) grade sugar alcohol.

In an embodiment of the invention the sugar alcohol comprises a non-DC (non-direct compressible) grade sugar alcohol.

In an embodiment of the invention the solid oral nicotine formulation is substantially free of mono- and disaccharides.

In an embodiment of the invention, the solid oral nicotine formulation is sugar-free. Thus, in this embodiment, the formulation does not comprise any sugar.

In an embodiment of the invention the solid oral nicotine formulation comprises high intensity sweetener.

In an embodiment of the invention, the high intensity sweetener is selected from sucralose, aspartame, salts of acesulfame, such as acesulfame potassium, alitame, saccharin and its salts, cyclamic acid and its salts, glycyrrhizin, dihydrochalcones, thaumatin, monellin, stevioside, and any combination thereof.

In an embodiment of the invention, the solid oral nicotine formulation comprises no more than 0.2% by weight of high intensity sweetener, such as no more than 0.1% by weight of high intensity sweetener.

In an advantageous embodiment of the invention, the solid oral nicotine formulation comprises flavor.

In an advantageous embodiment of the invention the solid oral nicotine formulation comprises flavor.

The flavor may advantageously be used as taste masking for the nicotine.

Furthermore, the flavor may advantageously promote increased salivation, whereby the dissolution of the inorganic cations may increase and/or which may increase the effect of the inorganic divalent cations on the nicotine release.

In an advantageous embodiment of the invention, the solid oral nicotine formulation comprises flavor in an amount of 0.1 to 15.0% by weight, such as 0.1 to 10.0% by weight, such as 0.1 to 5.0% by weight, such as 0.1 to 3% by weight.

In an advantageous embodiment of the invention, the solid oral nicotine formulation comprises no more than 0.5% by weight of flavor, such as no more than 0.2% by weight of flavor, such as no more than 0.1% by weight of flavor.

In an embodiment of the invention, the solid oral nicotine formulation comprises flavor in an amount of 0.1 to 15.0% by weight, such as 0.1 to 10.0% by weight, such as 0.1 to 5.0% by weight.

In an advantageous embodiment of the invention, the solid oral nicotine formulation is a non-tobacco formulation.

In an advantageous embodiment of the invention, the solid oral nicotine formulation comprises less than 2.0% by weight of tobacco, such as less than 1.0% by weight of tobacco, such as less than 0.5% by weight of tobacco, such as 0.0% by weight of tobacco.

In an advantageous embodiment of the invention, the solid oral nicotine formulation is provided as a formulation selected from the group consisting of powdered formulation, chewing gum, lozenge, chewable tablet, orally disintegrating tablet, fast disintegrating tablet, hard boiled dosage form, orodispersible film.

In an advantageous embodiment of the invention, the solid oral nicotine formulation is a tablet.

In an embodiment of the invention the solid oral nicotine formulation is provided as a tablet, such as lozenge, chewable tablet, an orally disintegrating tablet, a fast disintegrating tablet, or a chewing gum.

In an advantageous embodiment of the invention, the solid oral nicotine formulation is selected from the group consisting of a lozenge, a chewable tablet, or a chewing gum.

In an advantageous embodiment of the invention, the solid oral nicotine formulation is made by compression.

In an embodiment of the invention the solid oral nicotine formulation is made by compression.

In an embodiment of the invention the solid oral nicotine formulation is made by direct compression.

In an advantageous embodiment of the invention, the solid oral nicotine formulation comprises gum base in an amount of between 5 and 95% by weight, such as between 10 and 95% by weight, such as between 20 and 95% by weight, such as between 25 and 60% by weight.

In an advantageous embodiment of the invention, the solid oral nicotine formulation is a chewing gum.

In an advantageous embodiment of the invention, the solid oral nicotine formulation is a compressed chewing gum.

In an advantageous embodiment of the invention, the solid oral nicotine formulation is a lozenge.

In an advantageous embodiment of the invention, the solid oral nicotine formulation comprises disintegrant in an amount of 0.5-25% by weight of the formulation, such as 1-10% by weight of the formulation.

The disintegrant may advantageously facilitate a rather low disintegration time of the solid oral nicotine formulation whereby dissolution of the salt is initiated, which may facilitate the release of nicotine.

In an advantageous embodiment of the invention, the disintegrant is selected from starch, pregelatinated starch, modified starch (including potato starch, maize starch, starch 1500, sodium starch glycolate and starch derivatives), cellulose, microcrystalline cellulose, alginates, and superdisintegrants, such as crosslinked cellulose (such as sodium carboxy methyl cellulose), crosslinked polyvinyl pyrrolidone (PVP), crosslinked starch, crosslinked alginic acid, natural superdisintegrants, low-substituted hydroxypropylcellulose (LHPC) and calcium silicate, and combinations thereof.

In an embodiment of the invention the disintegrant comprises cross-linked polyvinylpyrrolidone.

In an embodiment of the invention the disintegrant is cross-linked polyvinylpyrrolidone.

An advantage of using cross-linked polyvinylpyrrolidone, also known as crospovidone, as disintegrant, may be that it decreases the dependence of the disintegration time on the compression force while allowing rather low disintegration times.

In an advantageous embodiment of the invention, the solid oral nicotine formulation is a fast disintegrating tablet.

In an advantageous embodiment of the invention, the solid oral nicotine formulation comprises superdisintegrant in an amount of 1-15% by weight of the formulation.

In an advantageous embodiment of the invention the super disintegrants includes crosslinked polymers.

In an advantageous embodiment of the invention, the super disintegrants is selected from the group of croscarmellose sodium, crospovidone, and sodium starch glycolate.

In an advantageous embodiment of the invention, the super disintegrants is selected from the group of croscarmellose sodium, crospovidone, and sodium starch glycolate.

In an advantageous embodiment of the invention the disintegrant comprises crosslinked polyvinylpyrrolidone.

In an embodiment of the invention, the salt has a water-solubility of 5-500 grams per 100 mL of water measured at 25 degrees Celsius, atmospheric pressure and pH 7.0, such as 5-350 grams per 100 mL of water measured at 25 degrees Celsius, atmospheric pressure and pH 7.0.

In an embodiment of the invention, the divalent cations are selected from the group consisting of divalent cations of calcium and magnesium, and the salt comprises inorganic anions selected from the group consisting of chloride, bromide, sulfate, hydrogen carbonate, and any combination thereof.

In an embodiment of the invention, the divalent cations are selected from the group consisting of divalent cations of calcium and magnesium, and the salt comprises inorganic anions selected from the group consisting of chloride, bromide, sulfate, hydrogen carbonate, and any combination thereof.

In an embodiment of the invention, the divalent cations are selected from the group consisting of divalent cations of calcium and magnesium, and the salt comprises inorganic anions selected from the group consisting of chloride, bromide, sulfate, hydrogen carbonate, and any combination thereof.

In an embodiment of the invention, the divalent cations are selected from the group consisting of divalent cations of calcium and magnesium, and the salt comprises inorganic anions selected from the group consisting of chloride, bromide, sulfate, hydrogen carbonate, and any combination thereof, and the solid oral nicotine formulation comprises inorganic salt in an amount of between 0.1 and 15.0% by weight of the composition, such as between 0.1 and 10.0% by weight of the composition, such as between 0.5 and 10.0% by weight of the composition.

In an embodiment of the invention, the divalent cations are selected from the group consisting of divalent cations of calcium and magnesium, and the salt comprises inorganic anions selected from the group consisting of chloride, bromide, sulfate, hydrogen carbonate, and any combination thereof, and the solid oral nicotine formulation comprises inorganic salt in an amount of between 0.1 and 15.0% by weight of the composition, such as between 0.1 and 10.0% by weight of the composition, such as between 0.5 and 10.0% by weight of the composition.

In an embodiment of the invention, the divalent cations are selected from the group consisting of divalent cations of calcium and magnesium, and the salt comprises inorganic anions selected from the group consisting of chloride, bromide, sulfate, hydrogen carbonate, and any combination thereof, and the solid oral nicotine formulation comprises inorganic salt in an amount of between 0.1 and 15.0% by weight of the composition, such as between 0.1 and 10.0% by weight of the composition, such as between 0.5 and 10.0% by weight of the composition.

In an embodiment of the invention, the solid oral nicotine formulation comprises nicotine-ion exchange combination in an amount of between 0.1 and 20% by weight, and the ion exchange resin is polacrilex resin.

In an embodiment of the invention, the solid oral nicotine formulation comprises nicotine-ion exchange combination in an amount of between 0.1 and 20% by weight, and the nicotine-ion exchange resin combination comprises nicotine in an amount of between 5 and 50% by weight.

In an embodiment of the invention, the solid oral nicotine formulation comprises nicotine-ion exchange combination in an amount of between 0.1 and 20% by weight, and the nicotine-ion exchange resin combination comprises nicotine in an amount of between 5 and 50% by weight and ion-exchange resin in an amount between 10 and 95% by weight.

In an embodiment of the invention, the solid oral nicotine formulation comprises nicotine-ion exchange combination in an amount of between 0.1 and 20% by weight, and the nicotine-ion exchange resin combination comprises nicotine in an amount of between 5 and 50% by weight, and the ion exchange resin is polacrilex resin.

In an embodiment of the invention, the solid oral nicotine formulation comprises nicotine-ion exchange combination in an amount of between 0.1 and 20% by weight, and the nicotine-ion exchange resin combination comprises nicotine in an amount of between 5 and 50% by weight and ion-exchange resin in an amount between 10 and 95% by weight, and the ion exchange resin is polacrilex resin.

In an embodiment of the invention, the solid oral nicotine formulation comprises nicotine-ion exchange combination in an amount of between 0.1 and 20% by weight, and the ion exchange resin comprises one or more resin(s) selected from the group consisting of:
 (i) a methacrylic, weakly acidic type of resin containing carboxylic functional groups,
 (ii) a copolymer of methacrylic acid and divinylbenzene, said copolymer containing carboxylic functional groups,
 (iii) a polystyrene, strongly acidic type of resin containing sulphonic functional groups,
 (iv) a polystyrene, intermediate acidic type of resin containing phosphonic functional groups, and
 (v) a combination thereof.

In an embodiment of the invention, the solid oral nicotine formulation comprises nicotine-ion exchange combination in an amount of between 0.1 and 20% by weight, and the nicotine-ion exchange resin combination comprises nicotine in an amount of between 5 and 50% by weight, and the ion exchange resin comprises one or more resin(s) selected from the group consisting of:
 (i) a methacrylic, weakly acidic type of resin containing carboxylic functional groups,
 (ii) a copolymer of methacrylic acid and divinylbenzene, said copolymer containing carboxylic functional groups,
 (iii) a polystyrene, strongly acidic type of resin containing sulphonic functional groups,
 (iv) a polystyrene, intermediate acidic type of resin containing phosphonic functional groups, and
 (v) a combination thereof.

In an embodiment of the invention, the solid oral nicotine formulation comprises nicotine-ion exchange combination in an amount of between 0.1 and 20% by weight, and the nicotine-ion exchange resin combination comprises nicotine in an amount of between 5 and 50% by weight and ion-exchange resin in an amount between 10 and 95% by weight, and the ion exchange resin comprises one or more resin(s) selected from the group consisting of:
 (i) a methacrylic, weakly acidic type of resin containing carboxylic functional groups,
 (ii) a copolymer of methacrylic acid and divinylbenzene, said copolymer containing carboxylic functional groups,
 (iii) a polystyrene, strongly acidic type of resin containing sulphonic functional groups,
 (iv) a polystyrene, intermediate acidic type of resin containing phosphonic functional groups, and
 (v) a combination thereof.

In an embodiment of the invention, the nicotine-ion exchange resin combination comprises free-base nicotine mixed with ion exchange resin, and the solid oral nicotine formulation comprises water in an amount of less than 5% by weight, such as less than 4% by weight, such as less than 3% by weight, such as less than 2% by weight.

In an embodiment of the invention, the nicotine-ion exchange resin combination consists of nicotine complexed with ion exchange resin, and the solid oral nicotine formulation is essentially free of water.

In an embodiment of the invention, the solid oral nicotine formulation further comprises a pH-regulating agent in an amount of 0.01 and 15% by weight, and the pH regulating agent is selected from the group consisting Sodium carbonate, Sodium bicarbonate, Potassium carbonate, and Magnesium carbonate; Potassium bicarbonate; trometamol; phosphate buffer, or any combination thereof.

In an embodiment of the invention, the at least one sugar alcohol is selected from xylitol, maltitol, mannitol, erythritol, isomalt, sorbitol, lactitol, and mixtures thereof, and the solid oral nicotine formulation comprises sugar alcohol in an amount of between 20% and 95% by weight, such as between 30 and 95% by weight, such as between 40 and 95% by weight, such as between 50 and 95% by weight.

In an embodiment of the invention, the solid oral nicotine formulation is a tablet, and the divalent cations are selected from the group consisting of divalent cations of calcium and magnesium, and the salt comprises inorganic anions selected from the group consisting of chloride, bromide, sulfate, hydrogen carbonate, and any combination thereof.

In an embodiment of the invention, the solid oral nicotine formulation is a tablet, and the divalent cations are selected from the group consisting of divalent cations of calcium and magnesium, and the salt comprises inorganic anions selected from the group consisting of chloride, bromide, sulfate, hydrogen carbonate, and any combination thereof.

In an embodiment of the invention, the solid oral nicotine formulation is a tablet, and the divalent cations are selected from the group consisting of divalent cations of calcium and magnesium, and the salt comprises inorganic anions selected from the group consisting of chloride, bromide, sulfate, hydrogen carbonate, and any combination thereof.

In an embodiment of the invention, the solid oral nicotine formulation is a chewing gum, and the divalent cations are selected from the group consisting of divalent cations of calcium and magnesium, and the salt comprises inorganic anions selected from the group consisting of chloride, bromide, sulfate, hydrogen carbonate, and any combination thereof.

In an embodiment of the invention, the solid oral nicotine formulation is a chewing gum, and the divalent cations are selected from the group consisting of divalent cations of calcium and magnesium, and the salt comprises inorganic anions selected from the group consisting of chloride, bromide, sulfate, hydrogen carbonate, and any combination thereof.

In an embodiment of the invention, the solid oral nicotine formulation is a chewing gum, and the divalent cations are selected from the group consisting of divalent cations of calcium and magnesium, and the salt comprises inorganic anions selected from the group consisting of chloride, bromide, sulfate, hydrogen carbonate, and any combination thereof.

In an embodiment of the invention, the solid oral nicotine formulation is a lozenge, and the divalent cations are selected from the group consisting of divalent cations of calcium and magnesium, and the salt comprises inorganic anions selected from the group consisting of chloride, bromide, sulfate, hydrogen carbonate, and any combination thereof.

In an embodiment of the invention, the solid oral nicotine formulation is a lozenge, and the divalent cations are selected from the group consisting of divalent cations of calcium and magnesium, and the salt comprises inorganic anions selected from the group consisting of chloride, bromide, sulfate, hydrogen carbonate, and any combination thereof.

In an embodiment of the invention, the solid oral nicotine formulation is a lozenge, and the divalent cations are selected from the group consisting of divalent cations of calcium and magnesium, and the salt comprises inorganic anions selected from the group consisting of chloride, bromide, sulfate, hydrogen carbonate, and any combination thereof.

In an embodiment of the invention the solid oral nicotine formulation is a chewing gum adapted to release at least 50% by weight of the nicotine after 10 minutes of chewing when the measurement is carried out in vitro using a chewing machine in accordance with European Pharmacopeia 4th. ed. 2.9.25, with a phosphate buffer with a pH of 7.4, such as at least 60% by weight of the nicotine after 10 minutes of chewing, such as at least 70% by weight of the nicotine after 10 minutes of chewing.

In an embodiment of the invention the solid oral nicotine formulation is a chewing gum adapted the release an amount of nicotine being 10 least % higher than a comparative chewing gum without divalent cations, when the measurement is carried out in vitro using a chewing machine in accordance with European Pharmacopeia 4th. ed. 2.9.25, with a phosphate buffer with a pH of 7.4.

The invention further relates to a solid oral nicotine formulation comprising
  a nicotine-ion exchange resin combination,
  and a salt comprising inorganic multivalent cations,
  wherein the salt has a water-solubility of at least 5 grams per 100 mL of water measured at 25 degrees Celsius, atmospheric pressure and pH 7.0.

In an advantageous embodiment of the invention, said multivalent cations are selected from the group consisting of multivalent ions of calcium, magnesium, zinc, aluminum, barium, iron, manganese, copper, lead, cobalt, nickel, such as $Ca^{2+}$, $Mg^{2+}$, $Zn^{2+}$, $Al^{3+}$, $Ba^{2+}$, $Fe^{2+}$, $Fe^{3+}$, $Fe^{4+}$, $Mn^{2+}$, $Mn^{4+}$, $Cu^{4+}$, or any combinations thereof.

In an embodiment of the invention, the multivalent cations are selected from the group consisting of $Ca^{2+}$, $Mg^{2+}$, $Zn^{2+}$, $Ba^{2+}$, $Fe^{2+}$, $Fe^{3+}$, $Fe^{4+}$, $Al^{3+}$, $Mn^{2+}$, $Mn^{4+}$, $Cu^{4+}$, and any combination thereof.

In an advantageous embodiment of the invention, the multivalent cations are selected from the group consisting of trivalent cations of aluminum, divalent cations of calcium, magnesium, iron, zinc, and any combination thereof.

In an embodiment the trivalent cation is aluminum.

In an embodiment of the invention, the multivalent cations are selected from the group consisting of aluminum chloride, divalent cations of calcium, magnesium, iron, zinc, and any combination there.

In an advantageous embodiment of the invention the multivalent cations are trivalent cations.

In an advantageous embodiment of the invention, the multivalent cations are selected from the group consisting of divalent cations of calcium, magnesium, iron, zinc, and any combination thereof.

In an embodiment of the invention, the solid oral nicotine formulation comprising a nicotine-ion exchange resin combination, and a salt comprising inorganic multivalent cations, wherein the salt has a water-solubility of at least 5 grams per 100 mL of water measured at 25 degrees Celsius, atmospheric pressure and pH 7.0, and wherein any of the above embodiment may combine to give new embodiments and/or combine with any of claims 1-60 without being limited to divalent cations.

DETAILED DESCRIPTION

When referring to amounts of an ingredient by terms such as "less than", "no more than", this generally refers to the particular ingredient being absent or present in a range from trace amounts to the specified maximum amount.

As used herein the term "nicotine" refers to nicotine used as a refined/isolated substance. Particularly, nicotine does not refer to tobacco materials having a content of nicotine. Thus, when referring to nicotine amounts also to be understood as the nicotine dose, the amounts refers to the amount of pure nicotine.

Nicotine also covers nicotine not obtained from tobacco, often referred to as synthetic nicotine.

As used herein, the term "nicotine-ion exchange resin combination" refer to a combination comprising nicotine complexed with ion exchange resin and/or free-base nicotine mixed with ion exchange resin.

As used herein, the term "nicotine complexed with ion-exchange resin" refers to nicotine bound to an ion exchange resin.

As used herein the term "free-base nicotine" refers to non-protonated form of nicotine, and therefore does not include nicotine salts and nicotine provided as a complex between nicotine and an ion exchange resin. Nevertheless, the free-base nicotine may be mixed with an amount of ion exchange resin. While free-base nicotine includes both free-base nicotine extracted from tobacco as well as synthetically manufactured free-base nicotine, the free-base nicotine is not provided in the form of tobacco or powdered tobacco. Typically, free-base nicotine is provided as a liquid.

In the present context the term "free-base nicotine mixed with ion exchange resin" refers to a mixture comprising free-base nicotine and ion exchange resin. It is noted that even if some embodiments comprise a combination of nicotine complexed with ion exchange resin and nicotine in its free-base form mixed with ion exchange resin, the term "free-base nicotine mixed with ion exchange resin" requires the presence of nicotine in its free-base form. In some embodiments, the mixture is an aqueous mixture. Free-base nicotine and water is mixed with ion-exchange resin, whereby a mixture comprising both free-base nicotine and ion exchange resin is obtained. Free-base nicotine mixed with ion exchange resin is referred to as "premix" in the examples.

As used herein, a molar ratio refers to the ratio of the molar content of the first component divided by the molar content of the second component.

The relative content between the first component and the second component may also be presented as equivalents of the first component relative to the second component. Thus, a solid oral nicotine formulation comprising divalent cations in a molar ratio of 0.1 relative to the amount of nicotine in the nicotine-ion exchange resin combination, may also be presented as a solid oral nicotine formulation comprising 0.1 eq. of divalent cations relative to the amount of nicotine in the nicotine-ion exchange resin combination, i.e. a solid oral nicotine formulation comprising 0.1 eq. of divalent cations and 1 eq. of nicotine in the nicotine-ion exchange resin combination.

As used herein, the term "release of nicotine" refers to the nicotine being made bioavailable, i.e. available for absorption over the mucous membrane in the oral cavity. While some forms of nicotine require dissolution for being bioavailable, other forms may be readily absorbed into the body without dissolution. For example, in order for the nicotine to be bioavailable, the matrix of the solid formulation should be broken, disintegrated or masticated. Some forms of nicotine require the nicotine to further be released from e.g. a carrier, e.g. nicotine from a nicotine-ion exchange resin such as nicotine polacrilex. Other nicotine forms, such as nicotine salts released from the carrier, readily dissolve upon disintegration of the solid oral formulation. Still, some nicotine forms may not require dissolving. This applies for e.g. nicotine free base, which is released upon disintegration of the solid oral formulation.

As used herein the term "fast release" may refer to the initial 2 minutes of the nicotine release period, whereas the term "sustained release" refers" to the subsequent period of the release period until end of experiment or end of use.

As used herein the term "fast release rate" refers to the released nicotine per minute within the initial 2 minutes.

As used herein the term "effective release" refers to the total release of nicotine over the release period of the experiment or the use period.

As used herein the term "water-soluble" refers to a relatively high water-solubility, for example a water-solubility of more than 5 gram of water-soluble composition or substance per 100 mL of water measured at 25 degrees Celsius, atmospheric pressure and pH of 7.0. Here, atmospheric pressure refers to a pressure of about 1 atmosphere, i.e. 101,325 Pascal (Pa) or a pressure within the range of 90,000 to 110,000 Pascal (Pa).

When referring to a "soluble" composition or substance, water-soluble is meant, unless otherwise stated.

As used herein, the term "FDT" (Fast Disintegrating Tablet) refers to a tablet which disintegrates in the oral cavity relatively fast from the administration, such as within about 60 seconds from oral administration.

As used herein the term "lozenge" refers to a tablet that dissolve or disintegrate slowly in the mouth, whereby its constituents are slowly released, e.g. pH regulating agents, flavor, nicotine etc. For example, a lozenge may dissolve within a period of at least 2 minutes upon oral administration, such as at least 3 minutes, such as at least 4 minutes, such as at least 5 minutes.

As used herein, the term "disintegrate" refers to a reduction of an object to components, fragments or particles. Disintegration time may be measured in vitro or in vivo. Unless otherwise stated, the in vitro measurements are carried out in accordance to European Pharmacopeia 9.0, section 2.9.1, Disintegration of tablets and capsules.

As used herein, the term "dissolve" is the process where a solid substance enters a solvent (such as oral saliva) to yield a solution.

As used herein, the term "pH regulating agent" refers to agents, which active adjust and regulates the pH value of the solution to which they have been added or are to be added. Thus, pH regulating agents may be acids and bases, including acidic buffering agents and alkaline buffering agents. On the other hand, pH regulating agents does not including substances and compositions that can only affect the pH by dilution. Furthermore, pH regulating agents does not include e.g. flavoring, fillers, etc.

As used herein the term "flavor" is understood as having its ordinary meaning within the art. Flavor includes liquid and powdered flavors. Thus, flavors do of course not include sweeteners (such as sugar, sugar alcohols and high intensity sweeteners), or acids providing pure acidity/sourness, nor compounds providing pure saltiness (e.g. NaCl) or pure bitterness. Flavor enhancers include substances that only provide saltiness, bitterness or sourness. Flavor enhancers thus include e.g. NaCl, Citric acid, ammonium chloride etc. The flavors can be natural or synthetic flavors.

Typically, the formulation comprises of ingredients selected from the group consisting of bulk sweeteners, fillers, gum base, flavors, binders, disintegrant, hereunder superdisintegrants, emulsifiers, antioxidants, pH regulating agents hereunder buffering agents, high intensity sweeteners, colors, glidants, lubricants, or any combination thereof.

In embodiments where the solid oral nicotine formulation comprises bulk sweeteners, different bulk sweeteners may be used. Bulk sweeteners include sugar sweetener and/or sugarless sweetener.

Sugar sweeteners generally include, but are not limited to saccharide-containing components, such as sucrose, dextrose, maltose, saccharose, lactose, sorbose, dextrin, trehalose, D-tagatose, dried invert sugar, fructose, levulose, galactose, corn syrup solids, glucose syrup, hydrogenated glucose syrup, and the like, alone or in combination.

Sugarless sweeteners generally include, but are not limited to sugar alcohols (also sometimes referred to as polyols) such as xylitol, maltitol, mannitol, erythritol, isomalt, sorbitol and lactitol.

The sweeteners may often support the flavor profile of the formulation.

In embodiments where the solid oral nicotine formulation comprises high intensity sweeteners, different high intensity sweeteners may be used.

Usable high intensity sweeteners include, but are not limited to sucralose, aspartame, salts of acesulfame, such as acesulfame potassium, alitame, saccharin and its salts, cyclamic acid and its salts, glycyrrhizin, dihydrochalcones, thaumatin, monellin, stevioside and the like, alone or in combination.

In embodiments where the solid oral nicotine formulation comprises fillers, different fillers may be used. Microcrystalline cellulose may be used as a filler in some embodiments of the invention.

Other usable fillers including as examples, magnesium and calcium carbonate, sodium sulphate, ground limestone, silicate compounds such as magnesium and aluminum silicate, kaolin and clay, aluminum oxide, silicium oxide, talc, titanium oxide, mono-, di- and tri-calcium phosphates, cellulose polymers, such as wood, starch polymers, fibers, plant fibers, such as wheat fiber, oat fiber, pea fiber, powdered cellulose, and combinations thereof.

In embodiments where the solid oral nicotine formulation comprises flavor, different flavors may be used.

Usable flavors including as examples almond, almond amaretto, apple, Bavarian cream, black cherry, black sesame seed, blueberry, brown sugar, bubblegum, butterscotch, cappuccino, caramel, caramel cappuccino, cheesecake (graham crust), cinnamon redhots, cotton candy, circus cotton candy, clove, coconut, coffee, clear coffee, double chocolate, energy cow, graham cracker, grape juice, green apple, Hawaiian punch, honey, Jamaican rum, Kentucky bourbon, kiwi, koolada, lemon, lemon lime, tobacco, maple syrup, maraschino cherry, marshmallow, menthol, milk chocolate, mocha, Mountain Dew, peanut butter, pecan, peppermint, raspberry, banana, ripe banana, root beer, RY 4, spearmint, strawberry, sweet cream, sweet tarts, sweetener, toasted almond, tobacco, tobacco blend, vanilla bean ice cream, vanilla cupcake, vanilla swirl, vanillin, waffle, Belgian waffle, watermelon, whipped cream, white chocolate, wintergreen, amaretto, banana cream, black walnut, blackberry, butter, butter rum, cherry, chocolate hazelnut, cinnamon roll, cola, creme de menthe, eggnog, English toffee, guava, lemonade, licorice, maple, mint chocolate chip, orange cream, peach, pina colada, pineapple, plum, pomegranate, pralines and cream, red licorice, salt water taffy, strawberry banana, strawberry kiwi, tropical punch, tutti frutti, vanilla, or any combination thereof.

According to an embodiment of the invention, flavor may be used as taste masking for the nicotine.

In an embodiment of the invention the solid oral nicotine formulation comprises gum base. The gum base may according to various embodiments comprise two or more ingredients selected from the group consisting of elastomers, resins, fillers, softener and waxes, or any combination thereof.

In an embodiment of the invention the solid oral nicotine formulation is a chewing gum tablet comprising gum base.

In preferred embodiments, the gum base comprises elastomers and resins, e.g. in an amount of at least 50% by weight of the gum base, such as at least 70% by weight of the gum base.

In embodiments of the invention, the gum base comprises elastomers and resins in amounts of at least 6% by weight of the chewing gum tablet, such as at least 15% by weight of the chewing gum tablet, or such as 6-50% by weight of the chewing gum tablet, such at 15-45% by weight of the chewing gum tablet.

As mentioned above, the gum base comprises resins in embodiments of the invention. The resins may be natural resins or synthetic resins, or a combination of natural resins and synthetic resins.

In some embodiments of the present invention, the gum base comprises for example
elastomer in the range of 1-15% by weight of the chewing gum tablet,
natural and/or synthetic resin in the range of 5-35% by weight of the chewing gum tablet, and
further other organic water insoluble components in the range of 5-30% by weight of the chewing gum tablet.

It is evident, that the overall total amount of these above gum base must be mutually adjusted in order to fit requirements with respect to tablet content of filler, sweetener, flavor, etc.

In some embodiments of the present invention, the chewing gum tablet comprises natural resins in an amount of 0.1 to 30%, such as 1 to 25%, such as 3 to 25% or 5 to 25%, by weight of the chewing gum tablet.

In some embodiments of the present invention, the chewing gum tablet comprises natural resins in an amount of at least 10% by weight of the chewing gum tablet.

In some embodiments of the present invention, the chewing gum tablet comprises natural resins in an amount of 10 to 30% by weight of the chewing gum tablet.

In some embodiments of the present invention, the chewing gum tablet is free of natural resins.

In embodiments of the present invention, the chewing gum tablet comprises synthetic resins in an amount of 0.1 to 30%, such as 1 to 25%, such as 3 to 25% or 5 to 25%, by weight of the chewing gum tablet.

As mentioned above, the gum base comprises elastomer in embodiments of the invention.

In embodiments of the present invention, the chewing gum tablet comprises elastomer in an amount of at least 2% by weight of the chewing gum tablet, such as at least 4% by weight of the chewing gum tablet.

In embodiments of the present invention, the chewing gum tablet comprises elastomer in an amount of less than 35% by weight of the chewing gum tablet, such as less than about 25% by weight of the chewing gum tablet, such as less than 20%, 15% or 10% by weight of the chewing gum tablet.

In embodiments of the present invention, the tablet comprises elastomer in an amount of 2-35% by weight of the tablet, such as 4-25% by weight of the tablet, such as 4-20% by weight of the tablet.

In an embodiment of the invention the gum base further comprises one or more selected form softeners, such as wax, fats, emulsifiers, and any combination thereof.

In embodiments of the present invention, the chewing gum tablet is provided with a coating.

In embodiments of the present invention, the chewing gum tablet has a weight in the range of 0.1 to 10 grams, such as in the range of 0.5 to 4 grams or such as in the range of 1.5 to 2.5 grams.

According to an embodiment of the invention, the chewing gum tablet may comprise filler. In embodiments of the present invention, the tablet comprises filler in an amount of 0.1 to 40% by weight of the chewing gum tablet.

Elastomers provide the rubbery, cohesive nature to the chewing gum tablet, which varies depending on this ingredient's chemical structure and how it may be compounded with other ingredients. Elastomers suitable for use in the chewing gum tablet of the present invention may include natural or synthetic types.

The elastomers employed in the tablet may vary depending upon various factors such as the desired texture of the coherent residual (i.e. the tablet after mastication) and the other components used in the formulation to make the chewing gum tablet. The elastomer may be any water-insoluble polymer known in the art. Illustrative examples of suitable polymers in the chewing gum tablet include both natural and synthetic elastomers. For example, those polymers which are suitable in the chewing gum tablet include, without limitation, natural substances (of vegetable origin) such as chicle gum, natural rubber, crown gum, nispero, rosidinha, jelutong, perillo, niger gutta, tunu, balata, gutta-percha, lechi capsi, sorva, gutta kay, and the like, and mixtures thereof. Examples of synthetic elastomers include, without limitation, styrene-butadiene copolymers (SBR), polyisobutylene, isobutylene-isoprene copolymers (i.e. butyl rubber), polyethylene, and the like, and mixtures thereof.

Natural resins may be used according to the invention and may be natural rosin esters, including as examples glycerol esters of partially hydrogenated rosins, glycerol esters of polymerized rosins, glycerol esters of partially dimerized rosins, glycerol esters of tally oil rosins, pentaerythritol esters of partially hydrogenated rosins, methyl esters of rosins, partially hydrogenated methyl esters of rosins, pentaerythritol esters of rosins, synthetic resins such as terpene resins derived from alpha-pinene, beta-pinene, and/or d-limonene, and natural terpene resins.

In an embodiment of the invention, the resin comprises terpene resins, e.g. derived from alpha-pinene, beta-pinene, and/or d-limonene, natural terpene resins, glycerol esters of gum rosins, tall oil rosins, wood rosins or other derivatives thereof such as glycerol esters of partially hydrogenated rosins, glycerol esters of polymerized rosins, glycerol esters of partially dimerised rosins, pentaerythritol esters of partially hydrogenated rosins, methyl esters of rosins, partially hydrogenated methyl esters of rosins or pentaerythritol esters of rosins and combinations thereof.

In an embodiment of the invention a synthetic resin may include polyvinyl acetate (PVAc) and/or vinyl acetate-vinyl laurate (VA-VL) copolymers.

In an embodiment of the invention, the chewing gum tablet may comprise one or more components selected from the group consisting of bulk sweeteners, flavors, dry-binders, tableting aids, anti-caking agents, emulsifiers, antioxidants, enhancers, absorption enhancers, high intensity sweeteners, softeners, colors, or any combination thereof.

In an embodiment of the invention, the chewing gum tablet comprises sweeteners, such as bulk sweeteners, sugar sweeteners, sugar substitute sweeteners, artificial sweeteners, high-intensity sweeteners, or any combination thereof.

Suitable bulk sweeteners include both sugar and non-sugar sweetening components.

Bulk sweeteners typically constitute from about 5 to about 95% by weight of the tablet, more typically about 20 to about 80% by weight such as 30 to 70% or 30 to 60% by weight of the chewing gum tablet.

Useful sugar sweeteners are saccharide-containing components commonly known in the chewing gum tablet art including, but not limited to, sucrose, dextrose, maltose, lactose, dextrins, trehalose, D-tagatose, dried invert sugar, fructose, levulose, galactose, corn syrup solids, and the like, alone or in combination.

As an example, sorbitol can be used as a non-sugar sweetener. Other useful non-sugar sweeteners include, but are not limited to, other sugar alcohols such as mannitol, xylitol, maltitol, isomalt, erythritol, lactitol and the like, alone or in combination.

High intensity artificial sweetening agents can also be used alone or in combination with the above sweeteners. For example, high intensity sweeteners include, but are not limited to sucralose, aspartame, salts of acesulfame, alitame, saccharin and its salts, cyclamic acid and its salts, glycyrrhizin, dihydrochalcones, thaumatin, monellin, stevioside (natural intensity sweetener) and the like, alone or in combination. In order to provide longer lasting sweetness and flavor perception, it may be desirable to encapsulate or otherwise control the release of at least a portion of the artificial sweeteners. Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided.

Usage level of the artificial sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (such as from about 0.02 to about 8% by weight). When carriers used for encapsulation are included, the usage level of the encapsulated sweetener will be proportionately higher.

Combinations of sugar and/or non-sugar sweeteners may be used in the chewing gum tablet formulation.

A chewing gum tablet according to the invention may, if desired, include one or more fillers/texturisers including as examples, magnesium, sodium sulphate, ground limestone, silicate compounds such as magnesium and aluminum silicate, kaolin and clay, aluminum oxide, silicium oxide, talc, titanium oxide, mono-, di- and tri-calcium phosphates, calcium and magnesium carbonate, cellulose polymers, such as wood or microcrystalline cellulose (MCC), and combinations thereof.

A number of further chewing gum tablet materials well known within the art may be applied within the scope of the present invention. Such components comprise but are not limited to waxes, fats, softeners, fillers, flavors, anti-oxidants, emulsifiers, colouring agents, binding agents and acidulants The granules or some of the granules may for example consist or largely comprise or consist of gum base and such granules may be manufactured by means of extrusion and under-water pelletizing.

The size of such granules of gum base may according to the present invention be controlled by several factors such as opening sizes, the composition, temperature and pressure drop, if a die plate is used in the extruder. Due to an interaction between the pressurized composition, temperature and friction in the openings of the die device, the average diameter of the produced granules is normally larger than the diameters of the openings in the die device. The relation between the diameters of the openings in the die device and the average diameters of granules produced from a specific composition may be determined by the skilled person on basis of routine experiments.

According to the invention it is also possible to produce granules with different average diameters by making granules with one diameter, and subsequently mix the granules with different average diameters in desired proportions.

Although the openings of a die of an extruder device may have cross-sections of any desired shape, e.g. circular, oval, square etc., it is in some embodiments preferred that the die device comprises openings with substantially circular cross-section and diameters in the range of 0.1 to 1.3 mm. A first set of openings can e.g. have a first diameter in the range of 0.07 to 0.7 mm, such as in the range of 0.15 to 0.6 mm, and suitably in the range of 0.2 to 0.5 mm. A second set of openings can have a second diameter larger than said first diameter. The second diameter is conveniently in the range of 0.4 to 1.3 mm, such as in the range of 0.7 to 1.2 mm.

In some embodiments the granulating system further comprises a drying device. Powder sweetener or talk may be added to the granules in a final drying step. The drying device can be a conventional centrifugal dryer or another suitable dryer e.g. a fluid bed dryer. The drying device can, for example, include a mixer. The powder sweetener may in an embodiment be sorbitol, which is mixed to the dried or partially dried granules. Minor amounts of residual moisture on the surface of the granules, e.g. 2% Wt. based on the total weight of the granules, may contribute to the adherence of the sorbitol powder to the surface of the granules. It is possible to use a conventional anti-agglomerating agent as e.g. talc, but sorbitol powder can function as an anti-agglomerating agent, and at the same time serves as sweetener. Although sorbitol is found to be most suitable, other bulk sweeteners based on polyols may also be suitable, e.g. mannitol, xylitol, maltitol, isomalt, erythritol, and lactitol.

In one embodiment the chewing gum tablet granulating system according to the invention further comprises one or more sieves adapted for removing granules with an average diameter such as above 1.3 mm. The removal of larger granules improves a subsequent tabletting process.

According to an embodiment of the invention at least the extruder and/or the die device comprises means for controlling the temperature of the composition. The means for controlling temperature can be cooling or heating devices, and may serve to facilitate the flow of composition through the extruder and the die device. In an embodiment the extruder comprises delivering means for delivering sweetener and/or flavour to the tablet composition in the extruder.

During extrusion of the composition the differential pressure between the composition in the extruder and the composition in the liquid filled chamber, i.e. over the die device is suitably above 10 bar, such as above 18 bar, such as in the range of 25 to 90 bar. The temperature of the composition in the extruder may for example be in the range of 40 to 125° C., suitably in the range 50 to 115° C. The temperature of the die device may for example be in the range of 60 to 250° C., suitably in the range 80 to 180° C. The temperature of the liquid in the liquid filled chamber is conveniently in the range of 8 to 40° C. The optimum for the pressures and temperatures in the method according to the invention may, however, may be determined by the skilled person as a matter of routine. The optimum values for specific compositions, varies of course, depending on the composition.

The quick cooling in the air filled or water-filled chamber may act to preserve possible fragile ingredients in the composition so that their qualities are better kept intact and conveyed into the granules included in the final product. This improved quality of the composition in the granules comprising the gum base improves the general composition of the tablet.

Granule fractions of different average weights may be produced with two different setups, each producing a batch of granules of a particular average weight, followed by a blending of the fractions. It is also possible to design a die means with die openings of at least two different sizes to simultaneously obtain granules with different average diameter. Thus, it is possible to obtain granules having different weights. More than two different average weights may be obtained, depending on the design of the die means in use. It is for instance possible to obtain granules with three, four or more different average weights.

The granules may be cut in a very large liquid-filled chamber, in which the granules are also cooled. In some embodiments the cooling is combined with transfer of the granules away from the chamber. This can be done e.g. by cooling the cut granules in water during transfer from the liquid filled chamber to a de-watering device. The transfer time from cutting to de-watering can be less than 6 s. The advantage of this is that water-soluble ingredients in the composition are not unnecessarily washed out of the granules. Optionally, the total time of contact between granules and cooling water can be further limited to less than 4 s.

The inventive chewing gum tablet may be formed by pressed particles and/granules. When these are tableted, bonds are established between the particles or granules, thereby conferring a certain mechanical strength to the tablet. Of the particles/granules, the tablet comprises calcium carbonate in an amount of more than 30% by weight of the tablet.

When pressure is applied to the particles/granules, the bulk volume is reduced and the amount of air is decreased. During this process energy is consumed. As the particles/granules come into closer proximity to each other during the volume reduction process, bonds may be established between the particles or granules. The formation of bonds is associated with a reduction in the energy of the system as energy is released.

Volume reduction takes place by various mechanisms and different types of bonds may be established between the particles or granules depending on the pressure applied and the properties of the particles or granules.

Examples of gum bases applicable for tablets of the present invention are described in the PCT/DK02/00461 and PCT/DK02/00462, hereby incorporated by reference.

The composition of gum bases, which are admixed with chewing gum tablet ingredients as defined below, can vary substantially depending on the particular product to be prepared and on the desired masticatory and other sensory characteristics of the final product. However, typical ranges (weight %) of the above water-insoluble components are:
  elastomer in the range of 1-15% by weight of the chewing gum tablet,
  natural and/or synthetic resin in the range of 5-35% by weight of the chewing gum tablet,
  filler in the range of 0-15% by weight of the chewing gum tablet, and
  further gum base components in the range of 5-30% by weight of the chewing gum tablet.

It is evident, that the overall total amount of gum base must be mutually adjusted in order to fit requirements with respect to tablet content of filler, sweetener, flavor, etc.

Granulates of gum base may be manufactured according to conventional methods or e.g. those described in the PCT/DK02/00461 and PCT/DK02/00462, hereby incorporated by reference.

The composition of gum base formulations may vary substantially depending on the particular product to be prepared and on the desired masticatory and other sensory characteristics of the final product. However, for some embodiments, typical ranges (% by weight) of the above gum base components are: 5 to 80% by weight elastomeric compounds, 5 to 80% by weight elastomer plasticizers, 0 to 40% by weight of waxes, 5 to 35% by weight softener, 0 to 50% by weight filler, and 0 to 5% by weight of miscellaneous ingredients such as antioxidants, colorants, etc. The gum base may comprise about 5 to about 95 percent, by weight, of the chewing gum, more commonly the gum base comprises 10 to about 60 percent, by weight, of the gum.

According to an embodiment of the invention, the pouch composition may further comprise one or more additives.

In an embodiment of the invention, said additives are selected from the group consisting of bile salts, cetomacrogols, chelating agents, citrates, cyclodextrins, detergents, enamine derivatives, fatty acids, labrasol, lecithins, phospholipids, synthetic and natural surfactants, nonionic surfactants, cell envelope disordering compounds, solvents, steroidal detergents, chelators, solubilization agents, charge modifying agents, pH regulating agents, degradative enzyme inhibitors, mucolytic or mucus clearing agents, membrane penetration-enhancing agents, modulatory agents of epithelial junction physiology, vasodilator agents, selective transport-enhancing agents, or any combination thereof pH regulating agents include buffers.

In an embodiment of the invention, said additives are selected from the group consisting of cetylpyridinium chloride (CPC), benzalkonium chloride, sodium lauryl sulfate, polysorbate 80, Polysorbate 20, cetyltrimethylammonium bromide, laureth 9, sodium salicylate, sodium EDTA, EDTA, aprotinin, sodium taurocholate, saponins, bile salt derivatives, fatty acids, sucrose esters, azone emulsion, dextran sulphate, linoleic acid, labrafil, transcutol, urea, azone, nonionic surfactants, sulfoxides, sauric acid/PG, POE 23 lauryl ether, methoxysalicylate, dextran sulfate, methanol, ethanol, sodium cholate, Sodium taurocholate, Lysophosphatidyl choline, Alkylglycosides, polysorbates, Sorbitan esters, Poloxamer block copolymers, PEG-35 castor oil, PEG-hydrogenated castor oil, Caprocaproyl macrogol-8 glycerides, PEG-8 caprylic/capric, glycerides, Dioctyl sulfosuccinate, Polyethylene lauryl ether, Ethoxydiglycol, Propylene glycol, mono-di-caprylate, Glycerol monocaprylate, Glyceryl fatty acids ($C_8$-$C_{18}$) ethoxylated Oleic acid, Linoleic acid, Glyceryl caprylate/caprate, Glyceryl monooleate, Glyceryl monolaurate, Capryliccapric triglycerides, Ethoxylated nonylphenols, PEG-(8-50) stearates, Olive oil PEG-6, esters, Triolein PEG-6 esters, Lecithin, d-alpha tocopherol polyethylene glycol 1,000 succinate, Citric acid, Sodium citrate, BRIJ, Sodium laurate, 5-methoxysalicylic acid, Bile salts, Acetyl salicylate, ZOT, Docosahexaenoic acid, Alkylglycosides, Sodium glycocholate (GC-Na), Sodium taurocholate (TC-Na), EDTA, Choline salicylate, Sodium caprate (Cap-Na), N-lauryl-beta-D-maltopyranoside (LM), Diethyl maleate, Labrasol, Sodium salicylate, Mentol, Alkali metal alkyl sulphate, Sodium lauryl sulphate, Glycerin, Bile acid, Lecithin, phosphatidylcholine, phosphatidylserine, sphingomyelin, phophatidylethanolamine, cephalin, lysolecithin, Hyaluronic acid: alkalimetal salts, sodium, alkaline earth and aluminum, Octylphenoxypolyethoxyethanol, Glycolic acid, Lactic acid, Chamomile extract, Cucumber extract, Borage oil, Evening primrose oil, Polyglycerin, Lysine, Polylysine, Triolein, Monoolein, Monooleates, Monolaurates, Polydocanol alkyl ethers, Chenodeoxycholate, Deoxycholate, Glycocholic acid, Taurocholic acid, Glycodeoxycholic acid, Taurodeoxycholic acid, Sodium glycocholate, Phosphatidylcholine, Phosphatidylserine, Sphingomyelin, Phosphatidylethanolamine, Cephalin, Lysolecithin, Alkali metal hyaluronates, Chitosan, Poly-L-arginine, Alkyl glucoside, Saccharide alkyl ester, Fusidic acid derivatives, Sodium taurdihydrofusidate (STDHF), L-α-phosphatidylcholine Didecanoyl (DDPC), Nitroglycerine, nitropruside, NOC5 [3-(2-hydroxy-1-(methyl-ethyl)-2-nitrosohydrazino)-1-propanamine], NOC12 [iV-ethyl-2-(1-ethyl-hydroxy-2-nitrosohydrazino)-ethanamine, SNAP [S-nitroso-N-acetyl-DL-penicillamine, NOR1, NOR4, deacylmethyl sulfoxide, azone, salicylamide, glyceryl-1,3-diacetoacetate, 1,2-isopropylideneglycerine-3-acetoacetate), Amino acids, Amino acid salts, monoaminocarboxlic acids, Glycine, alanine, phenylalanine, proline, hydroxyproline, hydroxyamino acids, serine, acidic amino acids, aspartic acid, Glutamic acid, Basic amino acids, Lysine, N-acetylamino acids, N-acetylalanine, N-acetylphenylalanine, TM-acetylserine, N-acetylglycine, N-acetyllysine, N-acetylglutamic acid, N-acetylproline, N-acetylhydroxyproline, lactic acid, malic acid and citric acid and alkali metal salts thereof, pyrrolidonecarboxylic acids, alkylpyrrolidonecarboxylic acid esters, N-alkylpyrrolidones, proline acyl esters, sodium lauryl phosphate, sodium lauryl sulphate, sodium oleyl phosphate, sodium myristyl sulphate, polyoxyethylene alkyl ethers, polyoxyethylene alkyl esters, and caproic acid, alkylsaccharide, fusidic acid, polyethylene glycol, cetyl alcohol, polyvinylpyrrolidone, Polyvinyl alcohol, Lanolin alcohol, Sorbitan monooleate, Ethylene glycol tetraacetic acid, Bile acid conjugate with taurine, Cholanic acid and salts, Cyclodextran, Cyclodextrin, Cyclodextrin (beta), Hydroxypropyl-β-cyclodetran, Sulfobutylether-β-cyclodextran, Methyl-β-cyclodextrin, Chitosan glutamate, Chitosan acetate, Chitosan hydrochloride, Chitosan hydrolactate, 1-O-alkyl-2-hydroxy-sn-glycero-3-phosphocholine, 3-O-alkyl-2-acetoyl-sn-glycero-1-phosphocholine, 1-O-alkyl-2-O-acetyl-sn-glycero-3-phospho(N,N,N-trimethyl)hexanolamine, Propylene glycol, Tetradecylmaltoside (TDM), Sucrose dedecanoate.

In an embodiment of the invention the solid oral nicotine formulation comprises dissolution modifiers.

Usable dissolution modifiers include any of, but are not limited to, acacia, agar, alginic acid or a salt thereof, carbomer, carboxymethylcellulose, carrageenan, cellulose, chitosan, copovidone, cyclodextrins, ethylcellulose, gelatin, guar gum, hydroxyethyl cellulose, hydroxyethyl methylcellulose, hydroxypropyl cellulose, hypromellose, inulin, methylcellulose, pectin, polycarbophil or a salt thereof, polyethylene glycol, polyethylene oxide, polyvinyl alcohol, pullulan, starch, tragacanth, trehalose, xanthan gum and mixtures thereof.

In one embodiment, the dissolution modifiers included within the formulations of the present invention may be selected from the group consisting of alginic acid or a salt thereof, polycarbophil or a salt thereof, xanthan gum and mixtures thereof.

In an embodiment of the invention the solid oral nicotine formulation comprise binders.

Usable binders include but are not limited to microcrystalline cellulose, hydroxypropylmethyl cellulose (HPMC), hydroxypropyl cellulose (HPC), or a mixture thereof.

In an embodiment of the invention the solid oral nicotine formulation comprises glidant. Silicon dioxide may be used as a glidant. Other glidants usable for the formulation may also be used within the scope of the invention.

In an embodiment of the invention the solid oral nicotine formulation comprises lubricant. Magnesium stearate and/or sodium stearyl fumarate may be used as a lubricant. Other lubricants usable for the formulation may also be used within the scope of the invention.

In an embodiment of the invention, the solid oral nicotine formulation is provided with an outer coating.

In an embodiment of the invention, said outer coating is selected from the group consisting of hard coating, soft coating and edible film-coating or any combination thereof.

EXAMPLES

Example 1: Preparation of Nicotine Premixes

A 60 liter planetary Bear Varimixer mixer was charged with water, and nicotine was weighed and added. The mixer was stirred at low speed for 1 minute at ambient temperature. Then ion exchange resin Amberlite® IRP64 was weighed and added to the mixer. The mixer was closed, stirred at high speed for 5 minutes, opened and scraped down, if necessary. Finally the mixer was stirred for further 5 minutes at high speed. The total process time was 20 minutes.

Thereby, mixtures of nicotine and cation exchange resin were produced from the constituents stated in the below tables.

Premix I:

TABLE 1

Ingredients used to manufacture nicotine premix I (5.7% nicotine).
% water in obtained nicotine-resin composition: 71.4

| Constituent | Amount (kg) | Amount (%) |
|---|---|---|
| Nicotine | 1.0 | 5.7 |
| Water | 12.5 | 71.4 |
| Resin | 4.0 | 22.9 |
| Total | 17.5 | 100.0 |

Premix II:

TABLE 2

Ingredients used to manufacture nicotine premix II (13.2% nicotine).
% water in obtained nicotine-resin composition: 34.1.

| Constituent | Amount (kg) | Amount (%) |
|---|---|---|
| Nicotine | 1.08 | 13.2 |
| Water | 2.80 | 34.1 |
| Resin | 4.32 | 52.7 |
| Total | 8.20 | 100.0 |

Premix III:

TABLE 3

Ingredients used to manufacture nicotine premix III (18.5% nicotine). % water in obtained nicotine-resin composition: 7.5.

| Constituent | Amount (kg) | Amount (%) |
|---|---|---|
| Nicotine | 1.08 | 18.5 |
| Water | 0.44 | 7.5 |
| Resin | 4.32 | 74.0 |
| Total | 5.84 | 100.0 |

Premix IV:

TABLE 4

Ingredients used to manufacture nicotine premix IV (10% nicotine). % water in obtained nicotine-resin composition: 50.0.

| Constituent | Amount (kg) | Amount (%) |
|---|---|---|
| Nicotine | 1.08 | 10.0 |
| Water | 5.40 | 50.0 |
| Resin | 4.32 | 40.0 |
| Total | 10.8 | 100.0 |

Premix V:

TABLE 5

Ingredients used to manufacture nicotine premix V (20% nicotine). % water in obtained nicotine-resin composition: 31.5.

| Constituent | Amount (kg) | Amount (%) |
|---|---|---|
| Nicotine | 1.78 | 20.0 |
| Water | 2.80 | 31.5 |
| Resin | 4.32 | 48.5 |
| Total | 8.90 | 100.0 |

Premix VI:

TABLE 6

Ingredients used to manufacture nicotine premix VI (30% nicotine). % water in obtained nicotine-resin composition: 27.5.

| Constituent | Amount (kg) | Amount (%) |
|---|---|---|
| Nicotine | 3.05 | 30.0 |
| Water | 2.80 | 27.5 |
| Resin | 4.32 | 42.5 |
| Total | 10.17 | 100.0 |

Premix VII

TABLE 7

Ingredients used to manufacture nicotine premix VII (35% nicotine). % water in obtained nicotine-resin composition: 25.6.

| Constituent | Amount (kg) | Amount (%) |
|---|---|---|
| Nicotine | 3.83 | 35.0 |
| Water | 2.80 | 25.6 |
| Resin | 4.32 | 39.4 |
| Total | 10.95 | 100.0 |

Premix VIII:

TABLE 8

Ingredients used to manufacture nicotine premix VIII (42% nicotine).. % water in obtained nicotine-resin composition: 22.8.

| Constituent | Amount (kg) | Amount (%) |
|---|---|---|
| Nicotine | 5.15 | 42.0 |
| Water | 2.80 | 22.8 |
| Resin | 4.32 | 35.2 |
| Total | 12.27 | 100.0 |

Examples 2—Preparation of Lozenge 500 mg nicotine lozenges were made as outlined in below tables 9-10.

The compositions are prepared as follows. First, by pouring about half of the sugar alcohol into a mixing bowl, followed by the remaining ingredients except lubricant, and finally the remaining sugar alcohol. The ingredients are tumbled/mixed with a mixer (Turbula or Duma) for 4-10 min at 49 rpm.

A premade MgSt-Sugar alcohol mixture, made by mixing MgSt with about 5% of the sugar alcohol in a mixer (Turbula or Duma) for 1 min at 49 rpm, is added and the ingredients are further mixed for 1-2 min at 49 rpm.

The lubricated powder blend is transferred to the hopper of a tableting machine.

The lozenges are then compressed at a compression force of about 15-25 kN. Punch used: 10.00 mm, circular, shallow concave, D tooling.

The lozenges are manufactured on a lab scale machine, for example RIVA Piccola bi-layer tablet press. The tablet machine is commissioned by adjusting the fill depth and compression force so the weight and hardness of lozenges match the acceptance criteria. A pre-compression force could be included to avoid capping.

TABLE 9

Compositions of lozenges.

| Ex | L01 | L02 | L03 | L04 | L05 | L06 | L07 | L08 |
|---|---|---|---|---|---|---|---|---|
| Amount of nicotine | 4 mg | 4 mg | 4 mg | 4 mg | 2 mg | 1 mg | 6 mg | 8 mg |
| Divalent cations* | 1 eq | 1 eq | 1 eq | 1 eq | 1 eq | 1 eq | 1 eq | 1 eq |

TABLE 9-continued

Compositions of lozenges.

| Ex | L01 | L02 | L03 | L04 | L05 | L06 | L07 | L08 |
|---|---|---|---|---|---|---|---|---|
| Raw material | Content in weight percent | | | | | | | |
| Mannitol | 92.20 | — | — | — | 94.98 | 96.36 | 89.43 | 86.66 |
| Isomalt | — | 92.20 | — | — | — | — | — | — |
| Sorbitol | — | — | 92.20 | — | — | — | — | — |
| Maltitol | — | — | — | 92.20 | — | — | — | — |
| Buffer | 0.5 | 0.5 | 0.5 | 0.5 | 0.5 | 0.5 | 0.5 | 0.5 |
| NPR 16% | 5.00 | 5.00 | 5.00 | 5.00 | 2.50 | 1.25 | 7.50 | 10.00 |
| Calcium chloride* | 0.55 | 0.55 | 0.55 | 0.55 | 0.27 | 0.14 | 0.82 | 1.09 |
| Flavor | 1.0 | 1.0 | 1.0 | 1.0 | 1.0 | 1.0 | 1.0 | 1.0 |
| HIS | 0.25 | 0.25 | 0.25 | 0.25 | 0.25 | 0.25 | 0.25 | 0.25 |
| MgSt | 0.5 | 0.5 | 0.5 | 0.5 | 0.5 | 0.5 | 0.5 | 0.5 |
| Total | 100 | 100 | 100 | 100 | 100 | 100 | 100 | 100 |

*Divalent cations may be provided as a hydrated salt, such as dihydrate, tetrahydrate, hexahydrate etc. The weight % in the table are based on the non-hydrated salt. The divalent cations are presented as equivalents relative to nicotine in nicotine ion-exchange combination.

TABLE 10

Compositions of lozenges.

| Ex | L11 | L12 | L13 | L14 | L15 | L16 | L17 | L18 | L19 |
|---|---|---|---|---|---|---|---|---|---|
| Amount of nicotine | 4 mg | 4 mg | 4 mg | 4 mg | 4 mg | 4 mg | 4 mg | 4 mg | 4 mg |
| Divalent cations* | 1 eq | 1 eq | 1 eq | 1 eq | 1 eq | 1 eq | 1 eq | 1 eq | 1 eq |
| Raw material | Content in weight percent | | | | | | | | |
| Mannitol | 94.83 | 94.03 | 95.03 | 47.28 | 94.3 | 94.00 | 94.45 | 94.41 | 94.42 |
| Xylitol | — | — | — | 47.33 | — | — | — | — | — |
| Buffer | 0.25 | 1.0 | — | 0.5 | 0.5 | 0.5 | 0.5 | 0.5 | 0.5 |
| Premix VI | 2.67 | 2.67 | 2.67 | 2.67 | 2.67 | 2.67 | 2.67 | 2.67 | 2.67 |
| Magnesium chloride* | 0.47 | 0.47 | 0.47 | 0.47 | — | — | — | — | — |
| Calcium acetate* | — | — | — | — | 0.78 | — | — | — | — |
| Calcium lactate* | — | — | — | — | — | 1.08 | — | — | — |
| FeCl$_2$* | — | — | — | — | — | — | 0.63 | — | — |
| ZnCl$_2$* | — | — | — | — | — | — | — | 0.67 | — |
| AlCl$_3$* | — | — | — | — | — | — | — | — | 0.66 |
| Flavor | 1.0 | 1.0 | 1.0 | 1.0 | 1.0 | 1.0 | 1.0 | 1.0 | 1.0 |
| HIS | 0.25 | 0.25 | 0.25 | 0.25 | 0.25 | 0.25 | 0.25 | 0.25 | 0.25 |
| MgSt | 0.5 | 0.5 | 0.5 | 0.5 | 0.5 | 0.5 | 0.5 | 0.5 | 0.5 |
| Total | 100 | 100 | 100 | 100 | 100 | 100 | 100 | 100 | 100 |

*Divalent cations may be provided as a hydrated salt, such as dihydrate, tetrahydrate, hexahydrate etc. The weight % in the table are based on the non-hydrated salt. The divalent cations are presented as equivalents relative to nicotine in nicotine ion-exchange combination.

TABLE 11

Compositions of lozenges.

| Ex | L21 | L22 | L23 | L24 | L25 | L26 | L27 | L28 |
|---|---|---|---|---|---|---|---|---|
| Amount of nicotine | 4 mg | 4 mg | 4 mg | 4 mg | 4 mg | 4 mg | 4 mg | 4 mg |
| Divalent cations* | 0.5 eq | 2 eq | 3 eq | 4 eq | 0.5 eq | 2 eq | 3 eq | 4 eq |
| Raw material | Content in weight percent | | | | | | | |
| Mannitol | 92.47 | 91.66 | 91.11 | 90.57 | 94.80 | 93.99 | 93.44 | 92.90 |
| Buffer | 0.5 | 0.5 | 0.5 | 0.5 | 0.5 | 0.5 | 0.5 | 0.5 |
| NPR 16% | 5.00 | 5.00 | 5.00 | 5.00 | — | — | — | — |
| Premix VI | | | | | 2.67 | 2.67 | 2.67 | 2.67 |
| Calcium chloride* | 0.28 | 1.09 | 1.64 | 2.18 | 0.28 | 1.09 | 1.64 | 2.18 |

TABLE 11-continued

| | Compositions of lozenges. | | | | | | | |
|---|---|---|---|---|---|---|---|---|
| Ex | L21 | L22 | L23 | L24 | L25 | L26 | L27 | L28 |
| Flavor | 1.0 | 1.0 | 1.0 | 1.0 | 1.0 | 1.0 | 1.0 | 1.0 |
| HIS | 0.25 | 0.25 | 0.25 | 0.25 | 0.25 | 0.25 | 0.25 | 0.25 |
| MgSt | 0.5 | 0.5 | 0.5 | 0.5 | 0.5 | 0.5 | 0.5 | 0.5 |
| Total | 100 | 100 | 100 | 100 | 100 | 100 | 100 | 100 |

*Divalent cations may be provided as a hydrated salt, such as dihydrate, tetrahydrate, hexahydrate etc. The weight % in the table are based on the non-hydrated salt. The divalent cations are presented as equivalents relative to nicotine in nicotine ion-exchange combination.

Example 3—Preparation of Gum Base

The composition of a gum base is presented in Table 11.

TABLE 12

| | Gum base compositions. Amounts are given in wt-% of the gum base. | |
|---|---|---|
| Raw material | GB101 | GB101B |
| | Content in weight percent | |
| Elastomer (butyl rubber and polyisobutylene) | 16 | 10 |
| Resins (polyvinyl acetate (PVAc), VA-VL copolymers, ester gums and terpene resins) | 44 | 50 |
| Filler (talc, calcium carbonate) | 15 | 17 |
| Softeners (wax, fats, emulsifiers) | 25 | 23 |
| Total | 100 | 100 |

GB = Gum Base.

The preparation of gum base in this example is carried out by first adding a high-molecular weight elastomer, synthetic resin and filler to a heated (about 120° C.) and running z-blade mixer. After about twenty minutes of mixing, natural resin is added to the running mixer and mixing is continued for about five minutes followed by addition of further natural resin. After about five minutes of continued mixing, some softener and further elastomer are added to the running mixer, and mixing is continued for about five minutes before addition of further softener and antioxidant to the running mixer. Mixing is continued for about half an hour to one hour, and the final gum base mass is emptied from the mixer into coated or lined pans, extruded or cast into any desirable shape. Those skilled in the art will recognize that many variations of the above-described procedure may be followed.

Example 4—Preparation of Chewing Gum

In the present example, the gum base GB101 from example 3 was made into chewing gum CG101 with the composition as described in Table 12.

TABLE 13

| Amounts are given in % by weight of the chewing gum formulation. | | | | | | |
|---|---|---|---|---|---|---|
| Chewing gum | CG101 A | CG101 B | CG101 C | CG101 D | COMP CG1 | COMP CG2 |
| Amount of nicotine | 2 mg | 2 mg | 2 mg | 2 mg | 2 mg | 2 mg |
| Divalent cations* | 1 eq. | 1 eq. | 1 eq. | 5 eq. | — | — |
| Raw material | Content in weight percent | | | | | |
| GB101A | 42.00 | — | — | — | — | — |
| GB101B | — | 55.0 | 55.0 | 55.0 | 55.0 | 55.0 |
| Bulk Sweetener | 50.51 | 37.91 | 37.64 | 37.35 | 38.05 | 37.78 |
| Calcium chloride* | 0.14 | 0.14 | 0.14 | 0.70 | — | — |
| NPR (16%) | 1.25 | 1.25 | — | 1.25 | 1.25 | — |
| Premix II | — | — | 1.52 | — | — | 1.52 |
| Buffer | 3.00 | 3.00 | 3.00 | 3.00 | 3.00 | 3.00 |
| Flavor | 2.40 | 2.40 | 2.40 | 2.40 | 2.40 | 2.40 |
| High intensity sweeteners | 0.70 | 0.30 | 0.30 | 0.30 | 0.30 | 0.30 |
| Total | 100 | 100 | 100 | 100 | 100 | 100 |

CG = Chewing Gum

*Divalent cations may be provided as a hydrated salt, such as dihydrate, tetrahydrate, hexahydrate etc. The weight % in the table are based on the non-hydrated salt. The divalent cations are presented as equivalents relative to nicotine in nicotine ion-exchange combination.

Bulk sweetener may e.g. be sorbitol, xylitol, maltitol alone or in combination

Buffer may e.g. be sodium carbonate and optionally sodium hydrogen carbonate alone or in combination Flavor may e.g. be peppermint High intensity sweeteners may e.g. be sucralose, acesulfame-potassium, aspartame and combinations thereof.

A conventional mechanical mixing procedure is used. The gum base is added to a mixer provided with mixing means like e.g. horizontally placed Z-shaped arms. The mixer had been preheated to a temperature of up to approximately 50° C., and the other ingredients are added according to a specified time schedule. Obviously, the amount of ingredients used may be varied within the scope of the present invention.

The obtained chewing gums weighted about 1 grams.

The chewing gum formulation may optionally be coated by means of hard coating. The coating may e.g. be applied according to conventional coating methods.

Example 5—Preparation of Gum Base Pellets by Continuous Extrusion

Gum bases were prepared according to Example 3
The compositions of gum bases are presented in Table 14.

TABLE 14

Gum base compositions. Amounts are given in wt-% of the gum base.

| | Chewing gum | | | |
|---|---|---|---|---|
| Raw material | GB102 | GB103 | GB104 | GB105 |
| | Content in weight percent | | | |
| Elastomer (butyl rubber and polyisobutylene) | 15.0 | 10.0 | 15.0 | 12.0 |
| Natural resins (ester gums and terpene resins) | 20.0 | 25.0 | 25.0 | 20.0 |
| Synthetic resins (polyvinyl acetate (PVAc), VA-VL copolymers) | 15.0 | 15.0 | 10.0 | 18.0 |
| Filler (talc, )calcium carbonate | 24.9 | 24.9 | 24.9 | 24.9 |
| Softeners (wax, fats, emulsifiers) | 25.0 | 25.0 | 25.0 | 25.0 |
| Antioxidant | 0.1 | 0.1 | 0.1 | 0.1 |
| Total | 100 | 100 | 100 | 100 |

GB = Gum Base.

Each of the gum base compositions were fed directly to an extruder in a first opening.

The gum bases were fed individually to the extruder (Leistrits ZSE/BL 360 kw 104, available from GALA GmbH, Germany). The gum base was melted and extruded to a granulator comprising a die plate and a water-filled chamber (granulator A5 PAC 6, GALA GmbH, Germany) connected to a water system comprising a water supply for the granulator and centrifugal dryer (TWS 20, available from GALA GmbH, Germany).

The individual gum base compositions (GB103-GB106) of Table 13 were fed to the extruder with a feed rate of 250 kg/h and an extruder screw speed of 200 rpm. The gum base compositions were made in separate productions. The temperature in the composition at the feed end of the extruder was 100° C. and the temperature of the composition at the outlet of the extruder was 109° C. The composition was delivered by the extruder device to the inlet side of a die plate at a pressure of 36 bar. The composition was extruded through the die plate having a temperature of 200° C. and 1100 holes of a diameter of 0.3 mm. In the granulator chamber the extruded composition was cut to granules by a cutter with 13 blades mounted in star shape on a central axle rotating with a cutter speed of 2800 rpm. The granules were cooled and transported to the centrifugal dryer in water with a temperature of 17° C. and a flow rate of 22 m$^3$/h. The average cooling and transport time in water was approx. 90 seconds. The individual granules had an average weight of 0.002 g.

Example 6

Preparation of Compressed Chewing Gum with NPR

The composition of compressed chewing gum is presented in Table 14.

TABLE 15

Compressed chewing gum composition. Amounts are given in wt-% of the chewing gum formulation.

| Chewing gum | CG102 | CG103 | CG104 | CG105 | COMP-CG3 |
|---|---|---|---|---|---|
| Amount of nicotine | 4 mg | 4 mg | 4 mg | 4 mg | 4 mg |
| Divalent cations* | 1 eq | 1 eq | 1 eq | 1 eq | 1 eq |
| Raw material | Content in weight percent | | | | |
| GB102 | 32.00 | — | — | — | 32.00 |
| GB103 | — | 32.00 | — | — | — |
| GB104 | — | — | 32.00 | — | — |
| GB105 | — | — | — | 32.00 | — |
| Magnesium chloride* | 0.12 | 0.12 | 0.12 | 0.12 | — |
| NPR(16%) | 1.25 | 1.25 | 1.25 | 1.25 | 1.25 |
| Sorbitol | 21.50 | 21.50 | 21.50 | 21.50 | 21.50 |
| Acesulfame K | 0.10 | 0.10 | 0.10 | 0.10 | 0.10 |
| Aspartame | 0.20 | 0.20 | 0.20 | 0.20 | 0.20 |
| Buffer | 1.50 | 1.50 | 1.50 | 1.50 | 1.50 |
| Flavor | 1.50 | 1.50 | 1.50 | 1.50 | 1.50 |
| Xylitol | 41.83 | 41.83 | 41.83 | 41.83 | 41.95 |
| Total | 100 | 100 | 100 | 100 | 100 |

*Divalent cations may be provided as a hydrated salt, such as dihydrate, tetrahydrate, hexahydrate etc. The weight % in the table are based on the non-hydrated salt. The divalent cations are presented as equivalents relative to nicotine in nicotine ion-exchange combination.

The gum base granules obtained in Example 5 (GB102-GB105) were individually mixed in a standard mixer with tablet base material in the form of powder as outlined in Table 15.

Before pressing, the gum base granules were mixed with the tablet base material in the form of powder, the gum base granules passed a standard horizontal vibration sieve for removing any particles larger than 1.3 mm.

The obtained chewing gums weighed about 2 grams.

Example 7—Preparation of Compressed Chewing Gum with Nicotine Premix

The compositions of compressed chewing gum are presented in Table 15.

TABLE 16

Compressed chewing gum composition. Amounts are given in wt-% of the chewing gum formulation.

| Chewing gum | CG110 | CG111 | CG112 | CG112 |
|---|---|---|---|---|
| Amount of nicotine | 4 mg | 4 mg | 4 mg | 4 mg |
| Divalent cations* | 1 eq | 1 eq | 1 eq | 1 eq |
| Raw material | Content in weight percent | | | |
| GB102 | 32.00 | — | — | — |
| GB103 | — | 32.00 | — | — |
| GB104 | — | — | 32.00 | — |
| GB105 | — | — | — | 32.00 |
| Calcium chloride* | 0.14 | 0.14 | 0.14 | 0.14 |
| Premix VI | 0.67 | 0.67 | 0.67 | 0.67 |
| Sorbitol | 21.50 | 21.50 | 21.50 | 21.50 |
| Acesulfame K | 0.10 | 0.10 | 0.10 | 0.10 |
| Aspartame | 0.20 | 0.20 | 0.20 | 0.20 |
| Buffer | 1.50 | 1.50 | 1.50 | 1.50 |
| Flavor | 1.50 | 1.50 | 1.50 | 1.50 |
| Xylitol | 42.39 | 42.39 | 42.39 | 42.39 |
| Total | 100 | 100 | 100 | 100 |

*Divalent cations may be provided as a hydrated salt, such as dihydrate, tetrahydrate, hexahydrate etc. The weight % in the table are based on the non-hydrated salt. The divalent cations are presented as equivalents relative to nicotine in nicotine ion-exchange combination.

The gum base granules obtained in Example 5 (GB102-GB105) were individually mixed in a standard mixer with tablet base material in the form of powder as outlined in Table 16.

Before pressing, the gum base granules were mixed with the tablet base material in the form of powder, the gum base granules passed a standard horizontal vibration sieve for removing any particles larger than 1.3 mm.

The obtained chewing gums weighted about 2 grams.

Example 8—Preparation of Compressed Chewing Gum with Nicotine Premix

The compositions of compressed chewing gum are presented in Table 17.

TABLE 17

Compressed chewing gum composition. Amounts are given in wt-% of the chewing gum formulation.

| Chewing gum | CG 120 | CG 121 | CG 122 | CG 123 | CG 124 | CG 125 | CG 126 | CG 127 |
|---|---|---|---|---|---|---|---|---|
| Amount of nicotine | 4 mg | 4 mg | 4 mg | 4 mg | 4 mg | 4 mg | 4 mg | 4 mg |
| Divalent cations* | 1 eq | 1 eq | 1 eq | 1 eq | 1 eq | 1 eq | 1 eq | 1 eq |
| Raw material | Content in weight percent | | | | | | | |
| GB102 | 32.00 | 32.00 | 32.00 | 32.00 | 32.00 | 32.00 | 32.00 | 32.00 |
| Calcium chloride* | 0.14 | 0.14 | 0.14 | — | — | — | — | — |
| Calcium acetate* | — | — | — | 0.19 | — | — | — | — |
| Calcium lactate* | — | — | — | — | 0.27 | — | — | — |
| $FeCl_2$* | — | — | — | — | — | 0.15 | — | — |
| $ZnCl_2$* | — | — | — | — | — | — | 0.17 | — |
| $AlCl_3$* | — | — | — | — | — | — | — | 0.16 |
| Premix VI | — | — | — | 0.67 | 0.67 | 0.67 | 0.67 | 0.67 |
| Premix II | 1.52 | — | — | — | — | — | — | — |
| Premix VII | — | 0.57 | — | — | — | — | — | — |
| Premix VIII | — | — | 0.48 | — | — | — | — | — |
| Sorbitol | 21.50 | 21.50 | 21.50 | 21.50 | 21.50 | 21.50 | 21.50 | 21.50 |
| Acesulfame K | 0.10 | 0.10 | 0.10 | 0.10 | 0.10 | 0.10 | 0.10 | 0.10 |
| Aspartame | 0.20 | 0.20 | 0.20 | 0.20 | 0.20 | 0.20 | 0.20 | 0.20 |
| Buffer | 1.50 | 1.50 | 1.50 | 1.50 | 1.50 | 1.50 | 1.50 | 1.50 |
| Flavor | 1.50 | 1.50 | 1.50 | 1.50 | 1.50 | 1.50 | 1.50 | 1.50 |
| Xylitol | 41.54 | 42.49 | 42.58 | 42.34 | 42.26 | 42.38 | 42.36 | 42.37 |
| Total | 100 | 100 | 100 | 100 | 100 | 100 | 100 | 100 |

*Multivalent cations may be provided as a hydrated salt, such as dihydrate, tetrahydrate, hexahydrate etc. The weight % in the table are based on the non-hydrated salt. The divalent cations are presented as equivalents relative to nicotine in nicotine ion-exchange combination.

The gum base granules obtained in Example 5 (GB102-GB105) were individually mixed in a standard mixer with tablet base material in the form of powder as outlined in Table 17.

Before pressing, the gum base granules were mixed with the tablet base material in the form of powder, the gum base granules passed a standard horizontal vibration sieve for removing any particles larger than 1.3 mm.

The obtained chewing gums weighted about 2 grams.

Example 9—Preparation of Compressed Chewing Gum with NPR

The composition of compressed chewing gum is presented in Table 18.

TABLE 18

Compressed chewing gum composition. Amounts are given in wt-% of the chewing gum formulation.

| Chewing gum | CG 130 | CG 131 | CG 132 | CG 133 | CG 134 | CG 135 |
|---|---|---|---|---|---|---|
| Amount of nicotine | 4 mg | 4 mg | 4 mg | 4 mg | 4 mg | 4 mg |
| Divalent cations* | 0.5 eq | 0.25 eq | 1 eq | 0.5 eq | 0.5 eq | 0.5 eq |
| Raw material | Content in weight percent | | | | | |
| GB102 | 32.00 | 32.00 | 32.00 | 20.00 | 25.00 | 40.00 |
| Calcium chloride* | 0.07 | 0.04 | 0.14 | 0.07 | 0.07 | 0.07 |
| NPR (16%) | 1.25 | 1.25 | 1.25 | 1.25 | 1.25 | 1.25 |
| Sorbitol | 21.40 | 21.50 | 21.50 | 21.50 | 21.50 | 21.50 |
| Acesulfame K | 0.10 | 0.10 | 0.10 | 0.10 | 0.10 | 0.10 |
| Aspartame | 0.20 | 0.20 | 0.20 | 0.20 | 0.20 | 0.20 |
| Buffer | 1.50 | 1.50 | 1.50 | 1.50 | 1.50 | 1.50 |
| Flavor | 1.50 | 1.50 | 1.50 | 1.50 | 1.50 | 1.50 |
| Xylitol | 41.98 | 41.91 | 41.81 | 53.88 | 48.88 | 33.88 |
| Total | 100 | 100 | 100 | 100 | 100 | 100 |

*Divalent cations may be provided as a hydrated salt, such as dihydrate, tetrahydrate, hexahydrate etc. The weight % in the table are based on the non-hydrated salt. The divalent cations are presented as equivalents relative to nicotine in nicotine ion-exchange combination.

The gum base granules obtained in Example 5 (GB102-GB105) were individually mixed in a standard mixer with tablet base material in the form of powder as outlined in Table 18.

Before pressing, the gum base granules were mixed with the tablet base material in the form of powder, the gum base granules passed a standard horizontal vibration sieve for removing any particles larger than 1.3 mm.

The obtained chewing gums weighted about 2 grams.

Example 10—Preparation of Fast Disintegrating Tablet

In the present example six fast disintegrating tablets (FDT) with 1 mg nicotine are prepared with formulations as outlined in table 19. The fast disintegrating tablet is prepared with NPR (nicotine polacrilex resin). Punch used: 7.00 mm, circular, shallow concave, D tooling. Tablet weight: 100.0 mg.

TABLE 19

Fast disintegrating tablet compositions. Amounts are given in mg.

| | FDT(a) | FDT(b) | FDT(c) | FDT(d) | FDT(e) | FDT(f) |
|---|---|---|---|---|---|---|
| Amount of nicotine | 1 mg | 1 mg | 1 mg | 1 mg | 1 mg | 1 mg |
| Divalent cations* | 1 eq | 1 eq | 1 eq | 1 eq | 1 eq | 1 eq |
| Raw material | Content in weight percent | | | | | |
| NPR (16%) | 6.25 | 6.25 | 6.25 | 6.25 | 6.25 | 6.25 |
| Calcium chloride* | 0.68 | 0.68 | 0.68 | 0.68 | 0.68 | 0.68 |
| Microcrystalline cellulose | — | — | — | 40.17 | 40.17 | 40.17 |
| Mannitol | 77.27 | 77.27 | 77.27 | 36.10 | 36.10 | 36.10 |
| Crospovidone | 5.00 | — | — | 5.00 | — | — |
| Croscarmellose Sodium | — | 5.00 | — | — | 5.00 | — |
| Sodium Starch Glycolate | — | — | 5.00 | — | — | 5.00 |
| Peppermint | 4.00 | 4.00 | 4.00 | 4.00 | 4.00 | 4.00 |
| Menthol | 0.40 | 0.40 | 0.40 | 0.40 | 0.40 | 0.40 |
| Sucralose | 0.40 | 0.40 | 0.40 | 0.40 | 0.40 | 0.40 |
| Sodium carbonate | 5.00 | 5.00 | 5.00 | 5.00 | 5.00 | 5.00 |
| Silicon dioxide | — | — | — | 1.00 | 1.00 | 1.00 |
| Magnesium stearate | 1.00 | 1.00 | 1.00 | 1.00 | 1.00 | 1.00 |
| Total | 100.0 | 100.0 | 100.0 | 100.0 | 100.0 | 100.0 |

FDT = Fast disintegrating tablet.

*Divalent cations may be provided as a hydrated salt, such as dihydrate, tetrahydrate, hexahydrate etc. The weight % in the table are based on the non-hydrated salt. The divalent cations are presented as equivalents relative to nicotine in nicotine ion-exchange combination.

Raw materials are weighed from bags or buckets into separate weighing containers. All excipients are sifted through an 800 micrometer sieve into a stainless steel or plastic bin in the following order:

Half the filler/bulk sweetener

The API and all other excipients, except magnesium stearate

The remaining half of the filler/bulk sweetener

These are mixed in a Turbula mixer for 4-10 minutes at 25 RPM. Then lubricant, for example magnesium stearate is sifted through an 800 micrometer sieve into the mixing bin, and the lubrication is conducted by additional mixing for 1-2 minutes at 25 RPM. The fill level of the mixing bin is kept between 40% and 70%, according to standardized practice. The lubricated powder blend is transferred to the hopper of a tableting machine.

The fast disintegrating tablets are manufactured on a lab scale machine, for example RIVA Piccola bi-layer tablet press. The tablet machine is commissioned by adjusting the fill depth and compression force so the weight and hardness of lozenges match the acceptance criteria. A pre-compression force could be included to avoid capping.

TABLE 20

Suggested start up parameters.

| Parameter | Target value |
|---|---|
| Speed | 10-20 rpm |
| Weight of FDT | 100 mg +/− 5% |
| Compression force | 2-8 kN |
| Thickness | N/A* |
| Friability (100 rpm) | <1% |

*The design of punches is not fixed. As the curvature impacts thickness, the thickness is not a fixed target at this time of development.

The acceptance criteria for friability should be fulfilled so packaging of the resulting fast disintegrating tablets is possible, but in this embodiment, the bulk sweetener and or filler should have relatively good compressibility and still have fast disintegration. The fast disintegrating tablets according to the invention may comprise coloring agents. According to an embodiment of the invention, the fast disintegrating tablets may comprise color agents and whiteners such as FD&C-type dyes and lakes, fruit and vegetable extracts, titanium dioxide and combinations thereof.

Example 11—Release Experiment and Varying Salts

The release experiment was performed by adding an amount of NPR (16%) and varying equivalent of $CaCl_2$ to 900 mL of water corresponding to a nicotine concentration of 28 mg/L. The equivalents of $CaCl_2$ are relative to nicotine. The temperature of the water was 25 degrees Celsius throughout the experiment and stirring of 100 rpm was applied throughout the experiment. pH was measured at experiment start and end. The pH was in all experiments below 7.0 at both the start and end of the experiment.

A relative low nicotine concentration is used in order to reduce the impact of equilibrium on both the release rate and effective release of nicotine from the ion-exchange resin.

Samples were taken out at varying timepoints and analyzed for nicotine content using standard HPLC. The results are presented as percentage of nicotine released.

TABLE 21

Release of nicotine over time in the presence of varying salts and varying equivalents of salt.

| | Salt | | | | |
|---|---|---|---|---|---|
| Minutes | No Salt | 1 eq NaCl | 10 eq NaCl | 1 eq $CaCl_2$ | 10 eq $CaCl_2$ |
| | | | Released nicotine (%) | | |
| 1 | 12.4 | — | — | 46.3 | — |
| 2 | 15.9 | 24.4 | 43.8 | — | 80.3 |
| 3 | — | — | — | 58.4 | — |
| 4 | 18.1 | — | — | — | — |
| 8 | 20.2 | — | — | 69.2 | — |
| 11 | 20.9 | — | — | 72.6 | — |
| 13 | — | 28.1 | 51.9 | — | 89.9 |
| 14 | 21.8 | — | — | 75.0 | — |
| 17 | 22.4 | — | — | 76.5 | — |
| 20 | 23.1 | — | — | 78.2 | — |
| 23 | — | 29.9 | 52.9 | — | — |
| 25 | 24.0 | — | — | — | — |
| 30 | 24.8 | — | — | — | — |
| 33 | — | 30.1 | 54.5 | — | 90.4 |
| 35 | 25.7 | — | — | — | — |
| 40 | 26.5 | — | — | — | — |
| 45 | 27.2 | — | — | 81.1 | — |
| 60 | 28.8 | — | — | 82.0 | — |

Evaluation: the result shows that the presence of $CaCl_2$ significantly increases the release of nicotine from NPR. Increasing the amount of $CaCl_2$ result in an increased release of nicotine. The presence of $CaCl_2$ increases both the initial release rate and seems to also increase the effective release of nicotine.

Furthermore, the results show that NaCl has a much lower effect on the release of nicotine, thus high amount of NaCl are needed in order to achieve comparable release of nicotine in the presence of for example 1 eq. of $CaCl_2$.

Example 12—Release Experiment Using NPR and Varying Equivalents of $CaCl_2$

The release experiment was performed by adding NPR (16%) and varying equivalent of $CaCl_2$ to a volume of water corresponding to a nicotine concentration of 28 mg/L. The equivalents of $CaCl_2$ are relative to nicotine. The temperature of the water was 25 degrees Celsius throughout the experiment and stirring of 100 rpm was applied throughout the experiment. pH was measured at experiment start and end. The pH was in all experiments below 7.0 at both the start and end of the experiment.

A relative low nicotine concentration is used in order to reduce the impact of equilibrium on both the release rate and effective release of nicotine from the ion-exchange resin.

Samples were taken out at varying timepoints and analyzed for nicotine content using standard HPLC. The result is presented as percentage of nicotine released.

TABLE 22

Shows the percentage of nicotine released from NPR at different timepoints in the presence of varying equivalents of $CaCl_2$.

| | $CaCl_2$ | | | | | | | |
|---|---|---|---|---|---|---|---|---|
| Minutes | 0 eq | 0.1 eq | 0.25 eq | 0.5 eq | 0.75 eq | 1 eq | 2 eq | 4 eq |
| | | | | Released nicotine (%) | | | | |
| 1 | 12.4 | 17.7 | 25.0 | 30.5 | 38.5 | 46.3 | 55.1 | 59.1 |
| 2 | 15.9 | 22.0 | — | 39.7 | — | — | — | — |

TABLE 22-continued

Shows the percentage of nicotine released from NPR at different timepoints in the presence of varying equivalents of $CaCl_2$.

| | $CaCl_2$ | | | | | | | |
|---|---|---|---|---|---|---|---|---|
| Minutes | 0 eq | 0.1 eq | 0.25 eq | 0.5 eq | 0.75 eq | 1 eq | 2 eq | 4 eq |
| | | | Released nicotine (%) | | | | | |
| 3 | — | — | 33.9 | — | 51.7 | 58.4 | 68.3 | 71.8 |
| 4 | 18.1 | 24.3 | — | 46.1 | — | — | — | — |
| 5 | — | — | 38.6 | — | 59.3 | — | 74.6 | 76.8 |
| 7 | — | — | 42.4 | — | 64.0 | — | — | — |
| 8 | 20.2 | 26.6 | — | 53.3 | — | 69.2 | 78.7 | 79.9 |
| 9 | — | — | 43.3 | — | 66.7 | — | — | — |
| 11 | 20.9 | 27.8 | 44.1 | 56.4 | 68.9 | 72.6 | 81.1 | 82.4 |
| 13 | — | — | 46.0 | — | 71.0 | — | — | — |
| 14 | 21.8 | 28.7 | — | 58.9 | — | 75.0 | 82.7 | 83.9 |
| 15 | — | — | 45.9 | — | 73.0 | — | — | — |
| 17 | 22.4 | 29.3 | — | 61.0 | 74.4 | 76.5 | 83.8 | 84.7 |
| 18 | — | — | 47.2 | — | — | — | — | — |
| 20 | 23.1 | 30.3 | 47.5 | 62.4 | 76.3 | 78.2 | 85.0 | 85.0 |
| 25 | 24.0 | 31.1 | — | 64.4 | — | — | — | — |
| 30 | 24.8 | 31.8 | 49.3 | 65.8 | — | — | — | — |
| 35 | 25.7 | 32.6 | — | 66.8 | — | — | — | — |
| 40 | 26.5 | 33.2 | — | 67.8 | — | — | — | — |
| 45 | 27.2 | 33.8 | 50.6 | 69.2 | 80.2 | 81.1 | 87.3 | 87.3 |
| 60 | 28.8 | 35.0 | 51.7 | 69.2 | 81.1 | 82.0 | — | 88.1 |

Evaluation: the result shows that the presence of $CaCl_2$ significantly increases the release of nicotine from NPR. Increasing the amount of $CaCl_2$ result in an increased release of nicotine. The presence of $CaCl_2$ increases both the initial release rate and seems to also increase the effective release of nicotine.

Example 13—Release Experiment Using NPR and Varying Equivalents of $MgCl_2$

The release experiment was performed by adding NPR (16%) and varying equivalents of MgCl2 to a volume of water corresponding to a nicotine concentration of 28 mg/L. The equivalents of $MgCl_2$ are relative to nicotine. The temperature of the water was 25 degrees Celsius throughout the experiment and stirring of 100 rpm was applied throughout the experiment. pH was measured at experiment start and end. The pH was in all experiments below 7.0 at both the start and end of the experiment.

A relative low nicotine concentration is used in order to reduce the impact of equilibrium on both the release rate and effective release of nicotine from the ion-exchange resin.

Samples were taken out at varying timepoints and analyzed for nicotine content using standard HPLC. The result is presented as percentage of nicotine released.

TABLE 23

Shows the percentage of nicotine released from NPR at different timepoints in the presence of varying equivalents of $MgCl_2$.

| | $MgCl_2$ | | | | | | | |
|---|---|---|---|---|---|---|---|---|
| Minutes | 0 eq | 0.1 eq | 0.25 eq | 0.5 eq | 0.75 eq | 1 eq | 2 eq | 4 eq |
| | | | Released nicotine (%) | | | | | |
| 1 | 12.4 | 16.8 | 23.2 | 33.7 | 40.6 | 42.3 | 53.7 | 63.0 |
| 3 | — | 22.9 | 32.2 | 44.1 | 52.2 | 55.3 | 66.5 | 73.6 |
| 5 | — | 25.8 | 37.0 | 49.9 | 58.1 | 62.4 | 72.2 | 79.4 |
| 7 | — | 27.6 | 39.9 | 54.0 | 62.4 | 66.7 | 74.8 | 81.3 |
| 9 | — | 28.4 | 41.6 | 56.7 | 64.8 | 69.3 | 76.5 | 83.2 |
| 11 | 20.9 | 29.1 | 43.0 | 58.6 | 67.5 | 71.7 | 78.2 | 83.9 |

TABLE 23-continued

Shows the percentage of nicotine released from NPR at different timepoints in the presence of varying equivalents of $MgCl_2$.

| | $MgCl_2$ | | | | | | | |
|---|---|---|---|---|---|---|---|---|
| Minutes | 0 eq | 0.1 eq | 0.25 eq | 0.5 eq | 0.75 eq | 1 eq | 2 eq | 4 eq |
| | | | Released nicotine (%) | | | | | |
| 13 | — | 29.9 | 44.5 | 60.2 | 70.1 | 73.0 | 79.7 | 85.1 |
| 15 | — | 30.5 | 44.8 | 61.6 | 71.2 | 74.2 | 80.4 | 87.0 |
| 20 | 23.1 | 31.5 | 47.2 | 64.5 | 72.8 | 76.5 | 82.1 | 87.5 |
| 25 | 24.0 | 32.5 | 47.7 | 65.7 | 75.8 | 77.7 | 83.8 | 87.9 |
| 30 | 24.8 | 33.2 | 48.8 | 68.1 | 78.2 | — | — | 88.1 |

Evaluation: the result shows that the presence of $MgCl_2$ significantly increases the release of nicotine from NPR. Increasing the amount of $MgCl_2$ result in an increased release of nicotine. The presence of $MgCl_2$ increases both the initial release rate and seems to also increase the effective release of nicotine. The results are comparable to the result presented in example 12.

Example 14—Release Experiment Using 1 Equivalent of $CaCl_2$ and Nicotine Premix Having Varying Content of Nicotine The release experiment was performed by adding nicotine premix having varying content of nicotine and 1 equivalent of $CaCl_2$ to a volume of water, whereby a corresponding nicotine concentration of 28 mg/L is obtained. The equivalent of $CaCl_2$ is relative to nicotine. The temperature of the water was 25 degrees Celsius throughout the experiment and stirring of 150 rpm was applied throughout the experiment. pH was measured at experiment start and end. The pH was in all experiments below 7.0 at both the start and end of the experiment.

A relative low nicotine concentration is used in order to reduce the impact of equilibrium on both the release rate and effective release of nicotine from the ion-exchange resin.

Samples were taken out at varying timepoints and analyzed for nicotine content using standard HPLC. The result is presented as percentage of nicotine released.

TABLE 24

Shows the percentage of nicotine released from nicotine premix at different timepoints in the presence of 1 equivalent of $MgCl_2$.

Ingredients

| | Premix | | | | | | | |
|---|---|---|---|---|---|---|---|---|
| | II | II | VI | VI | VII | VII | VIII | VIII |
| | $CaCl_2$ | | | | | | | |
| Min. | — | 1 eq. | — | 1 eq. | — | 1 eq. | — | 1 eq. |
| | | | Released nicotine (%) | | | | | |
| 1 | 2.1 | 9.1 | 37.2 | 56.3 | 43.8 | 55.7 | 58.3 | 69.6 |
| 2 | 3.0 | 14.7 | 44.9 | 66.9 | 53.4 | 66.0 | 66.2 | 78.7 |
| 3 | 4.0 | 19.9 | 48.9 | 71.4 | 57.4 | 73.4 | 70.1 | 82.6 |
| 4 | 4.9 | 24.7 | 51.8 | 76.8 | 60.1 | 77.8 | 72.0 | 85.9 |
| 5 | 5.7 | 29.8 | 53.7 | 79.5. | 62.2 | 81.4 | 73.0 | 88.4 |
| 6 | 6.5 | 33.7 | 54.4 | 81.6 | 63.0 | 84.1 | 74.7 | 90.3 |
| 7 | 7.1 | 38.6 | 55.4 | 83.1 | 64.4 | 86.2 | 75.0 | 92.3 |
| 8 | 8.0 | 42.0 | 56.1 | 84.8 | 65.2 | 88.9 | 75.4 | 92.9 |
| 9 | 8.4 | 46.4 | 56.9 | 86.3 | 65.5 | 90.5 | 75.7 | 94.5 |
| 10 | 9.0 | 49.9 | 57.4 | 87.3 | 66.1 | 91.1 | 76.0 | 94.7 |
| 11 | — | 53.1 | 58.0 | 88.0 | 66.5 | 92.6 | 76.5 | 95.7 |
| 12 | — | 55.6 | 58.4 | 89.2 | 67.3 | 93.4 | — | 96.3 |
| 13 | — | 57.7 | 58.5 | 89.9 | 66.9 | 93.8 | 77.0 | 96.9 |

TABLE 24-continued

Shows the percentage of nicotine released from nicotine premix at different timepoints in the presence of 1 equivalent of MgCl₂.

Ingredients

| | Premix | | | | | | | |
|---|---|---|---|---|---|---|---|---|
| | II | II | VI | VI | VII | VII | VIII | VIII |
| | | | | CaCl₂ | | | | |
| Min. | — | 1 eq. | — | 1 eq. | — | 1 eq. | — | 1 eq. |
| | | | | Released nicotine (%) | | | | |
| 14 | — | 60.5 | 58.9 | 90.9 | 67.3 | 95.0 | — | 97.3 |
| 15 | 11.8 | 62.0 | 59.6 | 91.6 | 68.2 | 95.8 | 77.3 | 97.3 |

Evaluation: the result shows that the presence of CaCl₂ significantly increases the release of nicotine from premixes. The presence of CaCl₂ increases both the initial release rate and seems to also increase the effective release of nicotine. Furthermore, the results demonstrate that increasing the nicotine content of the premixes also increases the nicotine release.

Example 15—Release Experiment Using 1 Equivalent of AlCl₃ or 1 Equivalent of MgO (Comparative)

The release experiment was performed by adding NPR (16%) and 1 equivalent of AlCl₃ or 1 equivalent of MgO to a volume of water corresponding to a nicotine concentration of 28 mg/L. The equivalents are relative to nicotine. The temperature of the water was 25 degrees Celsius throughout the experiment and stirring of 150 rpm was applied throughout the experiment. pH was measured at experiment start and end. The pH was in all experiments below 7.0 at both the start and end of the experiment.

A relative low nicotine concentration is used in order to reduce the impact of equilibrium on both the release rate and effective release of nicotine from the ion-exchange resin.

Samples were taken out at varying timepoints and analyzed for nicotine content using standard HPLC. The result is presented as percentage of nicotine released.

TABLE 25

Shows the percentage of nicotine released from NPR at different timepoints in the presence of 1 equivalent of AlCl₃ or 1 equivalent of MgO.

| | Salt | | |
|---|---|---|---|
| Minutes | No Salt | 1 eq AlCl₃ | 1 eq MgO (comparative) |
| | Released nicotine (%) | | |
| 1 | 11.1 | 39.9 | 10.7 |
| 3 | 14.5 | 49.4 | 14.7 |
| 5 | 16.1 | 55.4 | 16.0 |
| 8 | 18.2 | 60.9 | 17.4 |
| 11 | 19.7 | 64.4 | 18.1 |
| 15 | 20.0 | 68.4 | 19.8 |
| 20 | 21.1 | 71.4 | 20.2 |
| 25 | 21.5 | 74.0 | 20.9 |
| 30 | 22.4 | 75.4 | 21.6 |

Evaluation: the results demonstrate that the presence of 1 equivalent of AlCl₃ significantly increases the release of nicotine from NPR. The presence of AlCl₃ increases both the initial release rate and seems to also increase the effective release of nicotine.

Furthermore, it is shown that the presence of MgO, having a water-solubility below 5 grams per 100 mL of water measured at 25 degrees Celsius, atmospheric pressure and pH 7.0, does not increase the release of nicotine in the release assay used here.

The invention claimed is:

1. A solid oral nicotine formulation comprising
   a nicotine-ion exchange resin combination,
   and a salt comprising inorganic divalent cations,
   wherein the salt is present as a separate component,
   wherein the solid oral nicotine formulation comprises divalent cations in molar ratio of 0.1 to 5 relative to the amount of nicotine in the nicotine-ion exchange resin combination,
   wherein the solid oral nicotine formulation is selected from the group consisting of a lozenge, a chewable tablet, and a chewing gum,
   wherein the ion exchange resin comprises a copolymer of methacrylic acid and divinylbenzene, said copolymer containing carboxylic functional groups, and
   wherein the salt is selected from the group consisting of calcium chloride and magnesium chloride, or combinations thereof.

2. The solid oral nicotine formulation according to claim 1, wherein the solid oral nicotine formulation comprises said salt in the amount of between 0.1 and 15.0% by weight of the composition.

3. The solid oral nicotine formulation according to claim 1, wherein the solid oral nicotine formulation comprises divalent cations in molar ratio of 0.25 to 5 relative to the amount of nicotine in the nicotine-ion exchange resin combination.

4. The solid oral nicotine formulation according to claim 1, wherein the solid oral nicotine formulation comprises inorganic salt in an amount of between 0.1 and 15.0% by weight of the composition.

5. The solid oral nicotine formulation according to claim 1, wherein the solid oral nicotine formulation comprises nicotine in an amount of at least 0.1 to 5.0% by weight.

6. The solid oral nicotine formulation according to claim 1, wherein the solid oral nicotine formulation comprises nicotine-ion exchange resin combination in an amount of between 0.1 and 20% by weight.

7. The solid oral nicotine formulation according to claim 1, wherein the ion exchange resin comprises polacrilex resin.

8. The solid oral nicotine formulation according to claim 1, wherein the nicotine-ion exchange resin combination comprises nicotine complexed with ion exchange resin.

9. The solid oral nicotine formulation according to claim 1, wherein the nicotine-ion exchange resin combination comprises free-base nicotine mixed with ion exchange resin.

10. The solid oral nicotine formulation according to claim 1, wherein the solid oral nicotine formulation comprises water in an amount of less than 5% by weight.

11. The solid oral nicotine formulation according to claim 1, wherein the solid oral nicotine formulation further comprises a pH-regulating agent in an amount of 0.01 and 15% by weight.

12. The solid oral nicotine formulation according to claim 1, wherein the solid oral nicotine formulation comprises at least one sugar alcohol.

13. The solid oral nicotine formulation according to claim 12, wherein the at least one sugar alcohol is selected from xylitol, maltitol, mannitol, erythritol, isomalt, sorbitol, lactitol, and mixtures thereof.

14. The solid oral nicotine formulation according to claim 1, wherein the solid oral nicotine formulation is a chewing gum.

15. The solid oral nicotine formulation according to claim 1, wherein the solid oral nicotine formulation is a lozenge.

16. The solid oral nicotine formulation according to claim 1, wherein the salt is calcium chloride.

17. The solid oral nicotine formulation according to claim 1, wherein the salt is magnesium chloride.

* * * * *